(12) United States Patent
Kwiatkowski et al.

(10) Patent No.: US 9,068,206 B1
(45) Date of Patent: Jun. 30, 2015

(54) SYSTEM FOR TREATMENT OF BIOMASS TO FACILITATE THE PRODUCTION OF ETHANOL

(75) Inventors: Jason Richard Kwiatkowski, Alton, IL (US); William F. McDonald, Utica, OH (US); David Charles Carlson, Yankton, SD (US)

(73) Assignee: Poet Research, Inc., Sioux Falls, SD (US)

( * ) Notice: Subject to any disclaimer, the term of this patent is extended or adjusted under 35 U.S.C. 154(b) by 456 days.

(21) Appl. No.: 12/716,989

(22) Filed: Mar. 3, 2010

Related U.S. Application Data

(60) Provisional application No. 61/157,143, filed on Mar. 3, 2009.

(51) Int. Cl.
  *C12P 17/10* (2006.01)

(52) U.S. Cl.
  CPC . *C12P 17/10* (2013.01); *Y02E 50/16* (2013.01)
  USPC .......................................................... 210/180

(58) Field of Classification Search
  CPC ................................ C12P 17/10; Y02E 50/16
  USPC ............. 210/198.2, 266, 692, 656, 180, 182, 210/190, 251, 253, 259, 269, 340, 664, 669, 210/683; 435/93, 163, 165, 289.1; 127/9, 127/46.2; 494/36
  See application file for complete search history.

(56) References Cited

U.S. PATENT DOCUMENTS

| | | | |
|---|---|---|---|
| 2,440,925 A | 5/1948 | Boeckeler |
| 3,940,492 A | 2/1976 | Ehnstrom |
| 4,009,074 A | 2/1977 | Walon |
| 4,092,434 A | 5/1978 | Yoshizumi et al. |
| 4,243,750 A | 1/1981 | Muller et al. |

(Continued)

FOREIGN PATENT DOCUMENTS

| | | |
|---|---|---|
| CA | 1143677 | 3/1983 |
| DE | 267508 | 5/1989 |

(Continued)

OTHER PUBLICATIONS de Mancilha et al, Evaluation of Ion Exchange Resins for Removal of Inhibitory Compounds from Corn Stover Hydrolyzate for Xylitol Fermentation, Aug. 2003, Biotechnology Progress, vol. 19, pp. 1837-1841.*

(Continued)

*Primary Examiner* — Matthew O Savage
(74) *Attorney, Agent, or Firm* — Kagan Binder, PLLC

(57) ABSTRACT

Systems for treating biomass for the production of ethanol are disclosed. The systems are configured to treat a liquid component separated from biomass to yield sugars available to be fermented into a fermentation product. The systems comprise a filter configured to remove particulate matter to provide a filtered component and an apparatus configured to remove inhibitors from the filtered liquid component provide a treated liquid component comprising sugars available for fermentation. Methods for treating for treating biomass useful in the production of a fermentation product are also disclosed. The methods include the steps of filtering a liquid component to remove particulate matter thereby yielding a filtered liquid component, and treating the filtered liquid component to remove inhibitors thereby yielding a treated liquid component comprising sugars available to be fermented into a fermentation product.

12 Claims, 17 Drawing Sheets

(56) References Cited

U.S. PATENT DOCUMENTS

| | | |
|---|---|---|
| 4,279,747 A | 7/1981 | Chen |
| 4,287,303 A | 9/1981 | Dahlberg et al. |
| 4,309,254 A | 1/1982 | Dahlstrom et al. |
| 4,316,956 A | 2/1982 | Lutzen |
| 4,358,536 A | 11/1982 | Thorsson et al. |
| 4,361,651 A | 11/1982 | Keim |
| 4,376,163 A | 3/1983 | Ehnstrom |
| 4,460,687 A | 7/1984 | Ehnstrom |
| 4,474,883 A | 10/1984 | Yamamoto et al. |
| 4,490,469 A | 12/1984 | Kirby et al. |
| 4,514,496 A | 4/1985 | Yoshizumi et al. |
| 4,522,920 A | 6/1985 | Thorsson et al. |
| 4,540,663 A | 9/1985 | Witt |
| 4,591,560 A | 5/1986 | Kainuma et al. |
| 4,618,579 A | 10/1986 | Dwiggins et al. |
| 4,716,218 A | 12/1987 | Chen et al. |
| 4,727,026 A | 2/1988 | Sawada et al. |
| 4,760,025 A | 7/1988 | Estell et al. |
| 4,863,864 A | 9/1989 | Ashikari et al. |
| 4,876,196 A | 10/1989 | Salzbrunn et al. |
| 4,933,279 A | 6/1990 | Carroll et al. |
| 5,061,497 A | 10/1991 | Thacker et al. |
| 5,084,385 A | 1/1992 | Ashikari et al. |
| 5,087,417 A | 2/1992 | Dumbroff et al. |
| 5,177,008 A | 1/1993 | Kampen |
| 5,177,009 A | 1/1993 | Kampen |
| 5,180,669 A | 1/1993 | Antrim |
| 5,231,017 A | 7/1993 | Lantero et al. |
| 5,250,182 A | 10/1993 | Bento et al. |
| RE34,606 E | 5/1994 | Estell et al. |
| 5,322,778 A | 6/1994 | Antrim et al. |
| 5,364,770 A | 11/1994 | Berka et al. |
| 5,407,580 A | 4/1995 | Hester et al. |
| 5,545,543 A | 8/1996 | Zinnamosca et al. |
| 5,559,031 A | 9/1996 | Zinnamosca et al. |
| 5,652,127 A | 7/1997 | Mitchinson et al. |
| 5,688,674 A | 11/1997 | Choi et al. |
| 5,721,127 A | 2/1998 | Deweer et al. |
| 5,721,128 A | 2/1998 | Deweer et al. |
| 5,736,375 A | 4/1998 | Deweer et al. |
| 5,736,499 A | 4/1998 | Mitchinson et al. |
| 5,756,714 A | 5/1998 | Antrim et al. |
| 5,817,498 A | 10/1998 | Deweer et al. |
| 5,824,532 A | 10/1998 | Barnett et al. |
| 5,849,549 A | 12/1998 | Barnett et al. |
| 5,958,739 A | 9/1999 | Mitchinson et al. |
| 5,981,237 A | 11/1999 | Meagher et al. |
| 6,074,854 A | 6/2000 | Deweer et al. |
| 6,136,576 A | 10/2000 | Diaz-Torres et al. |
| 6,171,817 B1 | 1/2001 | Berka et al. |
| 6,228,177 B1 | 5/2001 | Torget |
| 6,313,328 B1 | 11/2001 | Ulrich et al. |
| 6,409,841 B1 | 6/2002 | Lombard |
| 6,423,145 B1 | 7/2002 | Nguyen et al. |
| 6,451,063 B1 | 9/2002 | Clarkson et al. |
| 6,509,180 B1 | 1/2003 | Verser et al. |
| 6,538,182 B1 | 3/2003 | Thompson et al. |
| 6,616,948 B2 | 9/2003 | Gustavsson et al. |
| 6,664,095 B1 | 12/2003 | Suryanarayan et al. |
| 6,709,527 B1 * | 3/2004 | Fechter et al. ............... 127/46.2 |
| 6,774,284 B1 | 8/2004 | Thompson et al. |
| 6,803,218 B1 | 10/2004 | Seyfried et al. |
| 6,849,439 B2 | 2/2005 | Henson et al. |
| 6,849,782 B2 | 2/2005 | Thompson et al. |
| 6,855,529 B2 | 2/2005 | Thompson et al. |
| 6,867,237 B1 | 3/2005 | Taylor et al. |
| 6,872,316 B2 | 3/2005 | Heikkilä et al. |
| 6,878,860 B1 | 4/2005 | Thompson et al. |
| 7,077,953 B2 | 7/2006 | Ranney |
| 7,138,058 B2 | 11/2006 | Kurth et al. |
| 7,344,876 B2 | 3/2008 | Levine |
| 7,579,177 B2 | 8/2009 | Olsen et al. |
| 7,585,652 B2 | 9/2009 | Foody et al. |
| 8,287,652 B2 | 10/2012 | Heikkilä et al. |
| 8,815,552 B2 | 8/2014 | Narendranath et al. |

| | | |
|---|---|---|
| 2002/0164731 A1 * | 11/2002 | Eroma et al. .................. 435/163 |
| 2003/0134395 A1 | 7/2003 | Shetty et al. |
| 2003/0134396 A1 | 7/2003 | Shetty et al. |
| 2003/0180900 A1 | 9/2003 | Lanteo |
| 2003/0203454 A1 | 10/2003 | Chotani et al. |
| 2004/0023349 A1 | 2/2004 | Bisgaard-Frantzen et al. |
| 2004/0043117 A1 | 3/2004 | Cope et al. |
| 2004/0063184 A1 | 4/2004 | Grichko |
| 2004/0080923 A1 | 4/2004 | Janisch |
| 2004/0091983 A1 | 5/2004 | Veit et al. |
| 2004/0115779 A1 | 6/2004 | Olsen et al. |
| 2004/0157301 A1 | 8/2004 | Chotani et al. |
| 2004/0192896 A1 | 9/2004 | Finch |
| 2004/0197409 A1 | 10/2004 | Iyer et al. |
| 2004/0219649 A1 | 11/2004 | Olsen et al. |
| 2004/0234649 A1 | 11/2004 | Lewis et al. |
| 2005/0026261 A1 | 2/2005 | Otto et al. |
| 2005/0042737 A1 | 2/2005 | Vikso-Nielsen et al. |
| 2005/0100996 A1 | 5/2005 | Lantero, Jr. et al. |
| 2005/0136525 A1 | 6/2005 | Baldwin et al. |
| 2005/0203291 A1 | 9/2005 | Svenson et al. |
| 2005/0208623 A1 | 9/2005 | Baldwin et al. |
| 2005/0233030 A1 | 10/2005 | Lewis et al. |
| 2005/0239181 A1 | 10/2005 | Lewis et al. |
| 2006/0051847 A1 | 3/2006 | Gunnarsson et al. |
| 2006/0062889 A1 * | 3/2006 | Houston et al. ............... 426/634 |
| 2006/0246563 A1 | 11/2006 | Eroma et al. |
| 2007/0178567 A1 | 8/2007 | Lewis |
| 2007/0196907 A1 | 8/2007 | Lewis |
| 2007/0202214 A1 | 8/2007 | Lewis et al. |
| 2008/0032373 A1 | 2/2008 | Bhargava |
| 2008/0041366 A1 | 2/2008 | Wahnon |
| 2008/0056983 A1 | 3/2008 | Curren et al. |
| 2008/0102502 A1 | 5/2008 | Foody et al. |
| 2009/0053793 A1 | 2/2009 | Lefebvre et al. |
| 2010/0041116 A1 | 2/2010 | Lewis et al. |
| 2010/0151549 A1 | 6/2010 | Bhargava |
| 2010/0196980 A1 | 8/2010 | Smith et al. |
| 2010/0227369 A1 | 9/2010 | Narendranath et al. |
| 2010/0233771 A1 | 9/2010 | McDonald et al. |
| 2011/0070618 A1 | 3/2011 | Lewis et al. |
| 2011/0097446 A1 | 4/2011 | Lewis et al. |
| 2011/0111085 A1 | 5/2011 | Lewis et al. |
| 2011/0250312 A1 | 10/2011 | Lewis |
| 2012/0129234 A1 | 5/2012 | McDonald et al. |
| 2012/0178976 A1 | 7/2012 | Hennessey et al. |
| 2013/0065289 A1 | 3/2013 | Carlson |
| 2013/0143290 A1 | 6/2013 | Narendranath |
| 2013/0337521 A1 | 12/2013 | Carlson et al. |
| 2014/0024826 A1 | 1/2014 | Narendranath et al. |
| 2014/0209092 A1 | 7/2014 | McDonald et al. |
| 2014/0234911 A1 | 8/2014 | Narendranath et al. |

FOREIGN PATENT DOCUMENTS

| | | | |
|---|---|---|---|
| EP | 0138428 | 4/1985 | |
| EP | 0 171 218 | 2/1986 | |
| EP | 1 306 442 | 5/2003 | |
| GB | 2089836 | 12/1981 | |
| JP | 58-005145 | 1/1983 | |
| JP | 59-179093 | 10/1984 | |
| WO | WO 91/03543 | 3/1991 | |
| WO | WO 92/20777 | 11/1992 | |
| WO | WO 95/13362 | 5/1995 | |
| WO | WO 02/38787 | 5/2002 | |
| WO | WO 02/074895 | 9/2002 | |
| WO | WO 03/018766 | 3/2003 | |
| WO | WO 03/062430 | 7/2003 | |
| WO | WO03056038 A1 * | 7/2003 | ............. C13K 13/00 |
| WO | WO 03/066816 | 8/2003 | |
| WO | WO-2004/080923 A2 | 9/2004 | |
| WO | WO 2004/081193 | 9/2004 | |
| WO | WO-2004/106533 A1 | 12/2004 | |
| WO | WO 2005/052148 | 6/2005 | |
| WO | WO 2005/082155 | 9/2005 | |
| WO | WO 2005/099854 | 10/2005 | |

(56) References Cited

FOREIGN PATENT DOCUMENTS

| WO | WO 2011/159915 | 12/2011 |
|----|----------------|---------|
| WO | WO 2012/103281 | 8/2012  |

OTHER PUBLICATIONS

Nilvebrandt et al, Detoxification of Lignocellulose Hydrolysates with Ion-Exchange Resins, Mar. 2001, Applied Biochemistry and Biotechnology, vols. 91-93, pp. 35-49.*
Product Data Sheet for PUROLITE A103SPLUS Macroporous Weak Base Anion Exchange Resin, Jan. 2014.*
Abouzied et al., "Direct fermentation of potato starch to ethanol by cocultures of *Aspergillus niger* and *Saccharomyces cerevisiae*", Appl Environ Microbiol, 1986, 52(5):1055-9.
Aden et al., "Lignocellulolsic biomass to ethanol process design and economics utilizing co-current dilute acid prehydrolysis and enzymatic hydrolysis for corn stover", NREL, NREL-TP-510-32438, 2002, pp. 1-88 and Appendices A-G.
Aldrich, "New enzymes lower ethanol production fuel costs", BridgeNews, Kansas City, 2004.
Allison et al., "Transformation of the thermophilic fungus humicola grisea var. thermoidea and overproduction of humicola glucoamylase", Curr Genet, 1992, 21:225-229.
Argus Leader.Com., Web Page—Business—Broin Goes to Court, Printed Jun. 27, 2006, pp. 1-3.
Ashikari et al., "*Rhizopus* raw-starch-degrading glucoamylase: its cloning and expression in yeast", Agric. Bio. Chem., 1986, 50(4):957-964.
Author Unknown "Ready for Research", BioFuels Journal, pp. 20-23 (4Q04).
Author Unknown, "Chapter 1. Review of the literature—coproducts and near coproducts of fuel ethanol fermentation from grain", Agriculture and Agri-Food Canada Research Branch (Internet Mar. 2003).
Author Unknown, "Determination of acid a-Amylase activity, FIA", SOP No. EB-SM-0259.02/01 pp. 1-14 (Internet Mar. 2003).
Author Unknown, "Enzymatic modification of starch granules: peeling off versus porosity", TNO Nutrition and Food Research, Dec. 28, 2000, pp. 1-2.
Author Unknown, "Ethanol Fuels: The Clean Breeze", Date Unknown.
Author Unknown, "Grain processing enzymes for sweetener production", Genencor International. Apr. 2004, pp. 1-3.
Author Unknown, "NOVELOSE® resistant starch—the starch that thinks it's a fiber", National Starch and Chemical Compnay, 2003.
Author Unknown, "Nutrient composition of DDGS (100% dry matter basis) from various references—Table 1", Distillers Grains Quarterly, First Quarter 2006, pp. 27-28.
Author Unknown, "Resistant starch: the new generation of fiber," Functional Foods & Nutraceuticals, Sep./Oct. (Year Unknown), pp. 20-22.
Author Unknown, "SIU Edwardsville National corn to ethanol research pilot plant process description", Project No. 24307-78188, Washington group, Nov. 12, 2001.
Author Unknown, "Very high gravity technology", Ethanol Producer Magazine, Jan. 2006.
Bardini et al., "Continuous clarification of grape must by flotation," Vini d'italia, 1992, 34(1):31-38, Abstract.
Barr-Rosin. "Fluidised bed dryers and coolers." Gea. www.barr-rosin.com/english/pdf/fluid.pdf, Date Unknown.
Beesabathuni et al., "Effect of Corn Flour Particle Size on Ethanol Yield and Soluble Solids in Thin Stillage in a Dry Grind Process", American Society of Agricultural and Biological Engineers, Paper No. 036067, 2003.
Belya et al., "Composition of corn and distillers dried grains with solubles from dry grind ethanol processing", Bioresource Technology, 2004, 94:293-298.
Berven, "The Making of Broin Project", Ethanol Producer Magazine, Feb. 2005, pp. 66-71.

Biswas et al., "Analysis of Headspace Compounds of Distillers Grains using SPME in Conjunction with GC/MS and TGA", Journal of Cereal Science, 2001, 33:223-229.
Boel et al., "Glucoamylases G1 and G2 from *Aspergillus niger* are synthesized from two different but closely related mRNAs", The EMBO Journal, 1984, 3(5):1097-1102.
Bothast, "Ethanol research facility one of a kind," Industrial Oil Products Article, 2004, 15(8):518-519.
Brown et al., "The effect of temperature on the ehtanol tolerance of the yeast, *Saccharomyces uvarum* ", Biotechnology Letters, 1982, 4(4):269-274.
Bryan, "Changing the Game", Ethanol Producer Magazine, Aug. 2005, pp. 58-63.
Casey et al., "Reevaluation of Alcohol Synthesis and Tolerance on Brewer's Yeast", American Society of Brewing Chemists, Inc., 1985, 43(2):75-83.
Chen et al., "Comparison of four different chemical pretreatments of corn stover for enhancing enzymatic digestibility." Biomass and Bioenergy, 2009, 33:1381-1385.
Chen et al., "Effect of replacing helical glycine residues with alanines on reversible and irreversible stability and production of *Aspergillus awamori* glucoamylase", Protein Engineering, 1996, 9(6):499-505.
Chi et al., "High-concentration alcoholic production from hydrolysate of raw ground corn by a tetraploid yeast strain", Biotechnolgy Letters, 1993, 15(8):877-882.
Civil Docket for Case No. 4:04-cv-04202-LLP printed Jun. 23, 2006.
PCT/US04/07377 International Search Report dated Jun. 1, 2005.
PCT/US2005/008155 International Search Report Dated Nov. 30, 2005 and Written Opinion.
Daugulis et al., "The Economics of Ethanol Production by Extractive Fermentation", The Canadian Journal of Chemical Engineering, 1991, 69:488-497.
Dettori-Campus et al., "Hydrolysis of Starch Granules by the Amyase from *Bacillus stearothermophilus* NCA 26", Process Biochemistry, 1992, 27:17-21.
Dewitt-Dick et al., "A chemical free method of microbiological control in recirculating cooling water systems", Date Unknown.
District Court Civil Docket No. 1: Complaint, filed by Broin and Associates, Inc., Entered: Dec. 15, 2004.
District Court Civil Docket No. 102: Genencor'S Notice to Take Deposition of Novozymes North America, Inc., Entered May 2, 2005.
District Court Civil Docket No. 112: Transcript of Proceedings held on Mar. 4, 2005 regarding Docket No. 69, motion Hearing, Entered: May 13, 2005.
District Court Civil Docket No. 132: Memorandum Opinion and Order regarding Docket No. 54, denying in part Motion to Dismiss as to Counts III, IV, V, and VIII and granting without prejudice to Plaintiff's right to amend as to Counts VI and VII, denying Docket No. 54, Motion for a more Definite Statement Signed by Judge Lawrence L. Piersol on Jul. 26, 2005, Entered: Jul. 26, 2005.
District Court Civil Docket No. 138: Genencor International, Inc.'S Answer to Amended Complaint and Counterclaim against Broin and Associates, Inc., by Genencor International, inc. Entered: Aug. 29, 2005.
District Court Civil Docket No. 148: Reply to Docket No. 138, Answer to Amended Complaint and Counterclaim against filed by Broin and Associates, Inc., Broin and Associates, Inc. Entered: Sep. 20, 2005.
District Court Civil Docket No. 15-1: First Amended Complaint, filed by Broin and Associates, Inc. (Attachments: #1 Exhibit A—Press Release #2 Exhibit B—Magazine Article), Entered Jan. 25, 2005.
District Court Civil Docket No. 15-2: Press Release dated Nov. 4, 2004, Broin Companies Announces Ethanol Technology Revolution.
District Court Civil Docket No. 153: Memorandum in Support regarding Docket No. 152, Motion to dismiss First Amended Complaint Based on Intentional Violations of Protective Order filed by Genencor International, Inc. (Sanford, Steven) (Entered: Sep. 30, 2005).
District Court Civil Docket No. 16: First Motion to Expedite Discovery and Supporting Brief by Broin and Associates, Inc., Entered: Jan. 25, 2005.

(56) References Cited

OTHER PUBLICATIONS

District Court Civil Docket No. 17-1: Declaration of Jeffrey C. Brown regarding (16) First Motion to Expedite Discovery and Supporting Brief, Entered: Jan. 25, 2005.

District Court Civil Docket No. 17-6: Exhibit E of Docket No. 17, Plaintiff's First Set of Interrogatories to Defendant, Entered: Jan. 25, 2005.

District Court Civil Docket No. 50-1: Affidavit of Steven W. Sanford in Support of Defendant Genencor's Opposition to Motion for Summary Judgment, Entered Feb. 14, 2005.

District Court Civil Docket No. 50-6: Exhibit D of Docket No. 50, Jan. 10, 2005 letter from Mark Skoog to Ben Brown, Entered: Feb. 14, 2005.

District Court Civil Docket No. 52: Memorandum in Opposition regarding Docket No. 16, First Motion to Expedite Discovery and Supporting Brief, filed by Genencor International, Inc., Entered: Feb. 14, 2005.

District Court Civil Docket No. 53: Motion for Discovery, Requiring Plaintiff to Specify Trade Secrets Prior to Commencement of Discovery and Supporting Brief, b y Genencor International, Inc. Entered: Feb. 14, 2005.

District Court Civil Docket No. 54: Motion to Dismiss Pursuant to FRCP 12(b)(6); Motion for a More Definite Statement Pursuant to FRCP 12(e) and Supporting Brief, by Genencor International, Inc., Entered: Feb. 14, 2005.

District Court Civil Docket No. 61: Response to Motion regarding Docket No. 53, Motion for Discovery, Requiring Plaintiff to Specify Trade Secrets Prior to Commencement of Discovery and Supporting Brief, filed by Broin and Associates, Inc., Entered: Feb. 28, 2005.

District Court Civil Docket No. 62: Reply to Motion Response regarding Docket No. 16, First Motion to Expedite Discovery and Supporting Brief, filed by Broin and Associates, Inc., Entered: Mar. 1, 2005.

District Court Civil Docket No. 67: Reply to Motion Response regarding Docket No. 53, Motion for Discovery, Requiring Plaintiff to Specify Trade Secrets Prior to Commencement of Discovery and Supporting Brief, filed by Genencor International, Inc. Entered: Mar. 2, 2005.

District Court Civil Docket No. 68: Form 35 Report of parties Planning Meeting and Scheduling Information, Entered: Mar. 3, 2005.

District Court Civil Docket No. 77: Memorandum in Opposition regarding Docket No. 54, Motion to Dismiss Pursuant to FRCP 12(b)(6); Motion for a More Definite Statement Pursuant to FRCP 12(e) and Supporting Brief, filed by Broin and Associates, inc. Entered: Mar. 9, 2005.

District Court Civil Docket No. 85: Reply to Motion Response regarding Docket No. 54, Motion to Dismiss Pursuant to FRCP 12(b)(6); Motion for a More Definite Statement Pursuant to FRCP 12(e) and Supporting Brief, filed by Genencor International, Inc., Entered: Mar. 23, 2005.

District Court Civil Docket No. 90: Response to Docket No. 87 Brief, Regarding Genencor's Objections to Broin's Identification of Trade Secrets, filed by Broin and Associates, inc., Entered: Apr. 11, 2005.

District Court Civil Docket No. 95: Form 35 Report of Parties Planning Meeting and Scheduling information, Entered: Apr. 18, 2005.

Dong et al., "The Neutral Detergent Fiber, Acid Detergent Fiber, Crude Fiber, and Lignin Contents of Distillers' Dried Grains with Solubles", Journal of Food Science, 1987, 52(2):403-405.

Donohoe et al., "Detecting cellulase penetration into corn stover cell walls by immuno-electron microscopy", Biotechnology and Bioengineering, 2009, 103(3):480-489.

Dunn-Coleman et al., "Production of granular starch hydrolyzing enzymes for low energy grain ethanol production", 27th Symposium on Biotechnology for Fuels and Chemicals, Genencor International Presentation, (May 2005).

Elander et al., "Summary of findings from the Biomass Refining Consortium for Applied Fundamentals and Innovation (CAFI): corn stover pretreatment", Cellulose, 2009, 16:649-659.

Form PCT/ISA/206, Invitation to Pay Additional Fees and Partial International Search for International Patent Application PCT/US2006/017041, dated Sep. 15, 2006.

Fox, Fermentation and Biochemical Engineering Handbook Principles, Process Design, and Equipment, Second Edition, Vogel et al (eds.). Noyes Publications, Westwood, New Jersey, 1997, pp. 734-758.

Fujio et al., "Alcohol Fermentation of Raw Cassava Starch by *Rhizopus* koji without cooking", Biotechonolgy and Bioengineering, 1984, 26:315-319.

Genencor and Lantero patent application search USPTO site May 17, 2005.

Genencor Inventor Search, Oct. 3, 2005.

Gulati et al. 1996. Assessment of Ethanol Production Options for Corn Products. Bioresource Technology, vol. 58, pp. 253-264.

Hamdy et al., "Effects of virginiamycin on fermentation rate by yeast", Biomass and Bioenergy, 1996, 11(1):1-9.

Hamelinck et al., "Ethanol from lignocellulosic biomass: techno-economic performance in short-, middle- and long term", Biomass and Bioenergy, 2005, 28:384-410.

Han et al., "Saccharification and Ethanol Fermentation from Uncooked Starch Using *Aspergillus niger* Koji", Korean J. Food Sci. Technol., 1985, 17(4):258-264.

Han et al., "Amylolysis of Raw Corn by *Aspergillus niger* for Simultaneous Ethanol Fermentation", Biotechnology and Bioengineering, 1987, 30:225-232.

Hayashida et al., "High Concentration-Ethanol Fermantation of Raw Ground Corn", Agric. Biol. Chem., 1982, 46(7):1947-1950.

Hayashida et al., "Molecular cloning of Glucoamylase 1 Gene of *Aspergillus awamori* var. kawachi for Localization of the Raw-starch-affinity Site", Agric. Biol. Chem., 1989, 53(4):923-929.

Hayashida et al., "Raw Starch-digestive Glucoamulase Productivity of Protease-less Mutant from Asoergukkys awaniru var. kawachi", Agric. Biol. Chem., 1981, 45(12):2675-2681.

Islam et al., "Stability of virginiamycin and penicillin during alcohol fermentation", Biomass and Bioenergy, 1999, 17: 369-376.

Iwata et al. "Purification and Characterization of Rice a-glucosidase, a key enzyme for Alcohol Fermentation of Rice Polish", Journal of Bioscience and Bioengineering, 2003, 95(1):106-108.

Jacques et al., The Alcohol Textbook, 3rd Edition, A reference for the beverage, fuel and industrial alcohol industries, Nottingham University Press 1999, Alltech Inc. 1999 (386 pages).

Jacques et al., The Alcohol Textbook, 4th Edition, A reference for the beverage, fuel and industrial alcohol industries, Nottingham University Press 2003 Alltech Inc. 2003 (446 pages).

Jensen et al., "Purification of extracellular amylolytic enzymes from the Thermophilic fungus *Thermomyces lanuginosus* ", Can. J. Microbiol., 1988, 34:218-223.

Jones, "review: Biological principles for the effects of ethanol", Enzyme Microb. Technol., 1989, 11:130-153.

Joutsjoki et al., "A Novel Glucoamylase Preparation for Grain Mash Saccharification", Biotechnology Letters, 1993, 15(3):227-282.

Kang et al., "Effect of Initiation Factor eIF-5A Depletion on Protein Synthesis and Proliferation of *Saccharomyces cerevisiae*", J. Biol. Chem., 1994, 269(6):3934-3940.

Knott et al., "Effects of the Nutrient Variability of Distiller's Solubles and Grains within Ethanol Plants and the Amount of Distiller's Solubles Blended with Distiller's Grains on Fat, Protein and Phosphorus Content of DDGS", 2004.

Knott et al., "Variation in Particle Size and Bulk Density of Distiller's Dried Grains with Solubles (DDGS) Produced by "New Generation" Ethanol Plants in Minnesota and South Dakota", 2004.

Kuyper et al., "Evolutionary engineering of mixed-sugar utilization by a xylose-fermenting *Saccharomyces cerevisiae* strain", FEMS Yeast Research, 2005, 5:925-934.

Lang et al., "Recycle Bioreactor for Bioethanol Production from Wheat Starch II. Fermentation and Economics", Energy Sources, 2001, 23:427-436.

Lutzen, "Enzyme Technology in the Production of Ethanol—Recent Process Development", Advances in Biotechnology, vol. II: Fuels, Chemicals, Foods and Waste Treatment, 1981 Pergamon Pres Canada Ltd., pp. 161-167.

(56) References Cited

OTHER PUBLICATIONS

Makarov et al., "Quality improvement of table wines following continuous clarification treatments," Kharachova Promislovist, 1976, Abstract only.
Matsumoto et al., "Industrialization of a Noncooking System for Alcoholic Fermantation from Grains", Agric. Biol. Chem., 1982, 46(6):1549-1558.
Matsuoka et al., "Alcoholic Fermentation of Sweet Potato without Cooking", J. Ferment. Technol., 1982, 60(6):599-602.
McAloon et al., "Determining the Cost of Producing Ethanol from Corn Starch and Lignocellulosic Feedstocks", Technical Report NRELTP-580-28893, 2000, www.doe.gov/bridge.
McLean et al., "Fluorometric Method for Measuring Yeast Metabolic Activity", Technical Report, 2002, 3:5-25.
McLean et al., "A Novel Method for Quantitation of Active Yeast Cells", Technical Report, 2001, 2:1-5.
Mikuni et al., "Alcohol Fermentation of Corn Starch Digested by *Chalara paradoxa* Amylase without Cooking", Biotechnology and Bioengineering, 1987, 29:729-732.
Minnesota Pollution Control Agency, Ethanol Production in Minnesota. Air Quality/ General #1.20/ Oct. 2002, pp. 1-4.
Morris et al., "AFM Images of Complexes between Amylose and *Aspergillus niger* Glucoamylase Mutants, Native and Mutant Starch Binding Domains: A Model for the Action of glucoamylase", Starch/Starke, 2005, 57:1-7.
Naidu et al., "Effects of Particle Size Reduction on Saccharification in Dry Grind Corn Processing", Department of Agriculture of Biological Engineering, University of Illinois at Urbana Champaign, Poster Presentation 2002 or later.
Narendranath et al., "Acetic Acid Lactic Acid Inhibition of Growth of *Saccharomyces cerevisiac* b Different Mechanisms", American Society of Brewing Chemists, Inc., 2001, 59(4):187-194.
Narendranath et al., "Effect of yeast inoculation rate on the metabolism of contaminating lactobailli during fermentation of corn mash", J. Ind. Microbiol. Biotechnol., 2004, 31:581-584.
Narendranath et al., "Effects of acetic acid and lactic acid on the growth of *Saccharomyces cerevisiae* in minimal medium", Journal of Industrial Microbiology & Biotechnology, 2001, 26:171-177.
Narendranath et al., "Effects of *Lactobacilli* on Yeast-Catalyzed Ethanol Fermentations", Applied and Environmental Microbiology, 1997, 60(11):4158-4163.
Narendranath et al., "Urea Hydrogen Peroxide Reduces the Number of Laactobacilli, Nourishes Yeast, and Leaves No Residues in the Ethanol Fermentation", Applied and Environmental Microbiology, 2000, 66(10):4187-4192.
Narita et al., "Efficient Production of L-(+)-Lactic Acid from Raw Starch by *Streptococcus bovis* 148", Journal of Bioscience and Bioengineering, 2004, 97(6):423-425.
Neal St. Anthony, Columnists, "More profit, less waste from ethanol," Star & Tribune, Minneapolis, St. Paul, Minnesota, Date Unknown.
Nigam et al. 1995. Enzyme and microbial systems involved in starch processing. Enzyme and Microbial Technology, vol. 17, pp. 770-778.
Norman et al., "Process Considerations for the Production of Ethanol from Cereals", Novo Research Institute—Denmark, p. 1-15, Date Unknown.
Patent Title Word Search, Sep. 28, 2005.
PCT Patent Title Word Search, Genencor Assignee, Oct. 4, 2005.
Porter et al., "Variability in Soy Flour Composition", JAOCS, 2003, 80(6):557-562.
Pourbafrani et al., "Production of biofuels, limonene and pectin from citrus wastes", Bioresource Technology, 2010, 101:4246-4250.
Rosentrater, "Understanding Distillers Grain Storage, Handling and Flowability Challenges", Distillers Grain Quarterly, First Quarter 2006, pp. 18-21.
Saha et al., "Raw Starch Absorption, Elution and Digestion Behavior of Glucoamylase of *Rhizopus* niveus", J. Ferment. Technol., 1983, 61(1):67-72.
Schnier et al., "Translation Initiation Factor 5A and its Hypusine Modification are Essential for Cell Viability in the yeast *Saccharomyces cerevisiae*", Molecular and Cellular Biology, 1991, 11(6):3105-3114.
Shibuya et al., "Molecular Cloning of the Glucoamylase Gene of *Aspergillus shirousami* and its Expression in *Aspergillus oryzae*", Agric. Biol. Chem., 1990, 54(8):1905-1914.
Shurson, "The Effect of Nutrient Variability of Corn on Estimated Nutrient Variability of DDGS" University of Minnesota, Date Unknown.
Shurson, "The Value of High-Protein Distillers Coproducts in Swine Feeds", Distillers Grains Quarterly, First Quarter 2006, pp. 22.
Sigmund et al., "The Economics of Fair Play", Scientific American, 2002, pp. 83-87.
Singleton, P. et al., 1991. Dictionary of Microbiology and Molecular Biology, 1991. John Wiley and Sons. p. 964, col. I, II. 45-48.
Author Unknown, SpringerLink-Article, Web Page—Article—Natural Resources Research—"Ethanol Fuels: Energy Balance, Economics, and Enviornmental Impacts Are Negative", Printed Jul. 5, 2005, pp. 1-2.
Supplementary European Search Report Dated Sep. 21, 2010 in EP application 04719274.5.
Suresh et al., "Production of ethanol by raw starch hydrolysis and fermentation of damaged grains of wheat and sorghum", Bioprocess Engineering, 1999, 21:165-168.
Swanson, Company Spotlight, "Partnering in Progress", Ethanol Producer Magazine, 2004, pp. 62-64, 66-68.
Taylor et al., "Dry-Grind Process for Fuel Ethanol by Continuous Fermentation and Stripping", American Chemical Society and American Institute of Chemical Engineers, accepted for publication Mar. 27, 2000, p. A-G.
Taylor et al., "Some Properties of a Glucoamylase produced by the Thermophilic Fungus *Humicola lanuginose* ", Carbohydrate Research, 1978, 61:301-308.
Thammarutwasik et al., "Alcoholic Fermentation of Sorghum Without Cooking", Biotechnology and Bioengineering, 1986, 28:1122-1125.
Author Unknown, The fuel of the future, Novozymes (May 2002).
Thomas et al., "Fuel Alcohol Production: Effects of Free Amino Nitrogen on Fermentation of Very-High-Gravity Wheat Mashes", Applied and Environmental Microbiology, 1990, 56(7):2046-2050.
Tosi et al., "Purification and characterization of an extracellular glucoamylase from the thermophilic fungus *Humicola grisea* var. thermoidea", Can J. Microbiol., 1993, 39:846-852.
Tritto, "2 grants, 6 clients boost yields at ethanol center", St. Louis Business Journal, Nov. 26-Dec. 2, 2004.
Ueda et al., "Alchoholic Fermentation of Raw Starch without Cooking by Using Back-koji Amylase", J. Ferment. Technol., 1980, 58(3):237-242.
Ueda et al., "Direct hydrolysis of raw starch", Microbiological Sciences, 1984, 1(1):21-24.
Ueda, "Ethanol Fermentation of Starch Materials without Cooking", J. Jap. Soc. Starch Sci., 1982, 29(2):123-130, (English Abstract).
Van Maris et al., "Alcoholic fermentation of carbon sources in biomass hydrolysates by *Saccharomyces cerevisiae*: current status", Antonie van Leeuwenhoek, 2006, 90:391-418.
Van Uden et al., "Effects of ethanol on yeast performance; targets and underlying mechanisms". European Brewery Convention, Proceedings of the 19th Congress, London 1983, pp. 137-144.
Viitanen et al., "Production of a xylose utilizing *Zymomonas mobilis* strain for ethanol production from high concentrations of mixed sugars" 31st symposium on biotechnology for fuels and chemicals; San Francisco, CA May 2009, pp. 48-48.
Wang. "Argonne National Laboratory Ethanol Study: Key points." Office of Energy Efficiency and Renewal Energy—U.S. Department of Energy, pp. 1-3, 2005.
Weiss et al. "Distillers Grains", eXtension, Last Updated May 12, 2009, pp. 1-6, Printed May 8, 2010.
Weller et al., "Fuel Ethanol from Raw Corn by *Aspergilli* Hydrolysis with Concurrent Yeast Fermentation", Biotechnology and Bioengineering Symp., 1983, 13:437-447.

(56) References Cited

OTHER PUBLICATIONS

Yue et al., "Functionality of resistant starch in food applications", National Starch & Chemical (reprinted from Dec. 1998 issue of Food Australia) (1999).

Zheng et al., "Enzymatic saccharification of dilute acid pretreated saline crops for fermentable sugar production", Applied Energy, 2009, 86:2459-2465.

Ziffer et al., "Temperature Effects in Ethanol Fermentation High Corn Media", Biotechnology Letters, 1982, 4(12):809-814.

Jeffries, T.W., et al., Fermentation of Hemicellulosic Sugars and Sugar Mixtures by *Candida* shehatae, Biotechnology and Bioengineering, 31:502-506 (1988).

Taherzadeh, et al., Pretreatment of Lignocellulosic Wastes to Improve Ethanol and Biogas Production: A Review, Int. J. Mol. Sci., 9:1621-1651 (2008).

US Office Action dated May 7, 2012 in related U.S. Appl. No. 12/717,002.

US Office Action dated Jun. 20, 2012 in related U.S. Appl. No. 12/581,076.

US Office Action dated Sep. 4, 2012 in related U.S. Appl. No. 12/717,015.

US Office Action dated Aug. 1, 2012 in related U.S. Appl. No. 12/716,984.

US Office Action dated Mar. 13, 2012 in related U.S. Appl. No. 12/944,618.

U.S. Appl. No. 12/827,948, filed Jun. 2010, Bootsma et al.

U.S. Appl. No. 13/209,170, filed Aug. 2011, Bly et al.

U.S. Appl. No. 14/459,977, filed Aug. 2014, Bootsma.

U.S. Appl. No. 14/465,177, filed Aug. 2014, Narendranath et al.

Kearney, M., "*Industrial Membrane Filtration and Short-Bed Fractal Separation Systems for Separating Monomers from Heterogeneous Plant Material*", Amalgamated Research Inc., Dec. 2004. 83 pages.

Weng, Y., et al., "*Separation of acetic acid from xylose by nanofiltration*", Separation and Purification Technology 67 (2009); pp. 95-102.

U.S. Appl. No. 14/601,956, filed Jan. 2015, Kwiatkowski et al.

Yong, Xu, et al., *Membrane Separation Detoxification of Dilute-Acid Pretreatment Solution for Lignocellulosic Materials,* Abstracts of Dissertation of the $9^{th}$ Chinese Forestry Youth Academic Annual Conference, Session 5, (Dec. 31, 2010): pp. 210-211; including Human Translation.

\* cited by examiner

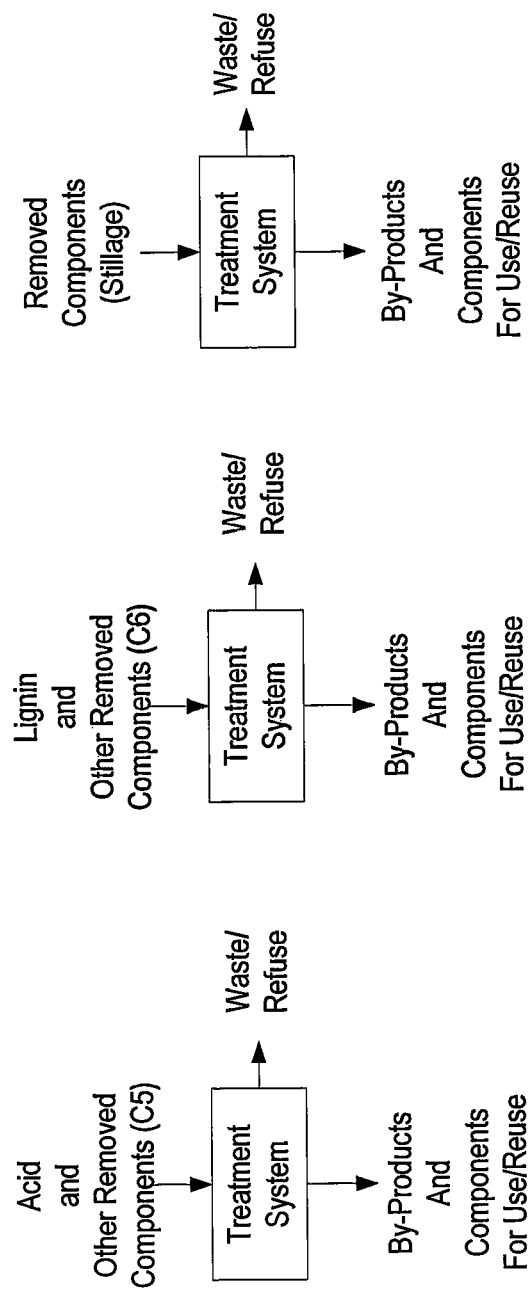

SYSTEM FOR TREATMENT OF BIOMASS TO FACILITATE THE PRODUCTION OF ETHANOL

CROSS-REFERENCE TO RELATED APPLICATIONS

The present application claims priority to and incorporates by reference the following application: U.S. Provisional Application Ser. No. 61/157,143, titled Removal of Inhibitors from Pentose Liquor Using Ion Exchange Chromatography, filed on Mar. 3, 2009.

The present application relates to and incorporates by reference U.S. application Ser. No. 12/716,984, titled System for Pre-Treatment of Biomass for the Production of Ethanol, filed on Mar. 3, 2010.

FIELD

The present invention relates to a system for treatment of biomass to be used in the production of ethanol. The present invention also relates to systems and methods for treating a component of lignocellulosic biomass comprising sugars to be fermented into cellulosic ethanol. The present invention further relates to a system for treating a component of lignocellulosic biomass that has been pre-treated and separated to remove inhibitors from the component prior to fermentation in order to facilitate pentose fermentation resulting in an efficient production of ethanol.

BACKGROUND

Ethanol can be produced from grain-based feedstocks (e.g. corn, sorghum/milo, barley, wheat, soybeans, etc.), from sugar (e.g. from sugar cane, sugar beets, etc.), and from biomass (e.g. from lignocellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter (grown for processing into bioproducts or for other purposes). In order to be used or processed, biomass will be harvested and collected from the field and transported to the location where it is to be used or processed.

In a conventional ethanol plant producing ethanol from corn, ethanol is produced from starch. Corn kernels are cleaned and milled to prepare starch-containing material for processing. (Corn kernels can also be fractionated to separate the starch-containing material (e.g. endosperm) from other matter (such as fiber and germ).) The starch-containing material is slurried with water and liquefied to facilitate saccharification where the starch is converted into sugar (e.g. glucose) and fermentation where the sugar is converted by an ethanologen (e.g. yeast) into ethanol. The product of fermentation (i.e. fermentation product) is beer, which comprises a liquid component containing ethanol and water and soluble components, and a solids component containing unfermented particulate matter (among other things). The fermentation product is sent to a distillation system. In the distillation system, the fermentation product is distilled and dehydrated into ethanol. The residual matter (e.g. whole stillage) comprises water, soluble components, oil and unfermented solids (i.e. the solids component of the beer with substantially all ethanol removed that can be dried into dried distillers grains (DDG) and sold as an animal feed product). Other co-products, for example syrup (and oil contained in the syrup), can also be recovered from the stillage. Water removed from the fermentation product in distillation can be treated for re-use at the plant.

In a biorefinery configured to produce ethanol from biomass, ethanol is produced from lignocellulosic material. Lignocellulosic biomass typically comprises cellulose, hemicellulose and lignin. Cellulose (a type of glucan) is a polysaccharide comprising hexose (C6) sugar monomers such as glucose linked in linear chains. Hemicellulose is a branched chain polysaccharide that may comprise several different pentose (C5) sugar monomers (such as xylose and arabinose) and small amounts of hexose (C6) sugar monomers in branched chains.

The biomass is prepared so that sugars in the lignocellulosic material (such as glucose from the cellulose and xylose from the hemicellulose) can be made accessible and fermented into a fermentation product from which ethanol can be recovered. After fermentation the fermentation product is sent to the distillation system, where the ethanol is recovered by distillation and dehydration. Other bioproducts such as lignin and organic acids may also be recovered as by-products or co-products during the processing of biomass into ethanol. Determination of how to more efficiently prepare and treat the biomass for production into ethanol will depend upon the source and type or composition of the biomass. Biomass of different types or from different sources is likely to vary in properties and composition (e.g. relative amounts of cellulose, hemicellulose, lignin and other components). For example the composition of wood chips will differ from the composition of corn cobs or switchgrass.

It would be advantageous to provide for a system for treating biomass to facilitate the production of ethanol. It would also be advantageous to provide for a system for treating a component of lignocellulosic biomass comprising sugars to be fermented into cellulosic ethanol. It would further be advantageous to provide for a system for treating a component of lignocellulosic biomass that has been pre-treated and separated to remove inhibitors from the component prior to fermentation in order to facilitate the efficient production of ethanol. It would further be advantageous to provide for a system that provides one or more features to facilitate improvement in the efficiency and yield of cellulosic ethanol from biomass.

SUMMARY

The present invention relates to a system for treating a liquid component separated from biomass comprising a filter configured to remove particulate matter from the liquid component thereby yielding a filtered liquid component. The system further comprises an apparatus configured to remove inhibitors from the filtered liquid component thereby yielding a treated liquid component comprising sugars available to be fermented into a fermentation product.

The present invention also relates to a system for treating a liquid component separated from biomass to yield sugars available to be fermented into a fermentation product comprising a filter configured to remove matter having a particle size of larger than about 25 to 100 microns from the liquid component and to provide a filtered component. The system further comprises an apparatus configured to remove inhibitors from the filtered liquid component by an ion exchange chromatography system and to provide a treated liquid component comprising sugars available for fermentation. The inhibitors comprise furfural, hydroxymethylfurfural (HMF), etc. The treated liquid component comprises furfural in an amount no greater than about 700 PPM.

The present invention further relates to a method for treating biomass useful in the production of a fermentation product comprising the steps of separating the biomass into a liquid component and a solids component, filtering the liquid component to remove particulate matter thereby yielding a filtered liquid component, and treating the filtered liquid component to remove inhibitors thereby yielding a treated liquid component comprising sugars available to be fermented into a fermentation product.

The present invention further relates to a method for treating a liquid component separated from biomass to yield sugars available to be fermented into a fermentation product comprising filtering the liquid component to remove particulate matter having a size of larger than about 100 microns and to provide a filtered liquid component. The method further comprises the step of treating the filtered liquid component using an ion exchange chromatography system to remove inhibitors and to provide a treated liquid component comprising sugars available for fermentation. The sugars in the treated liquid component comprise xylose and glucose. The inhibitors comprise furfural. The treated liquid component comprises furfural in an amount no greater than 700 PPM.

BRIEF DESCRIPTION OF THE FIGURES AND TABLES

FIGS. 4A, 4B and 4C are schematic block diagrams of systems for treatment and processing of components from the production of ethanol from biomass.

TABLES 1A and 1B list the composition of biomass comprising lignocellulosic plant material from the corn plant according to exemplary and representative embodiments.

TABLES 2A and 2B list the composition of the liquid component of pre-treated biomass according to exemplary and representative embodiments.

TABLES 3A and 3B list the composition of the solid component of pre-treated biomass according to exemplary and representative embodiments.

TABLE 4 presents the sugar (glucose and xylose) concentration and furfural binding capacity of the Dow® Optipore® SD-2 resin.

TABLE 5A presents the ion exchange system resin bed configuration according to Example 1A.

TABLE 5B presents the composition of the filtered liquid component supplied to the system and the composition of the samples of treated liquid component eluted from the system according to Example 1A.

TABLE 5C presents the ion exchange system resin bed configuration according to Example 1B.

TABLE 5D presents the composition of the filtered liquid component supplied to the system and the composition of the samples of treated liquid component eluted from the system according to Example 1B.

TABLE 5E presents the furfural, xylose and ethanol concentrations of the fractions and control according to Example 1B.

TABLE 5F presents the ion exchange system resin bed configuration according to Example 1C.

TABLE 5G presents the xylose concentration and furfural concentration in the ion exchange eluent and wash solutions according to various fractions according to Example 1C.

Figure 13A:
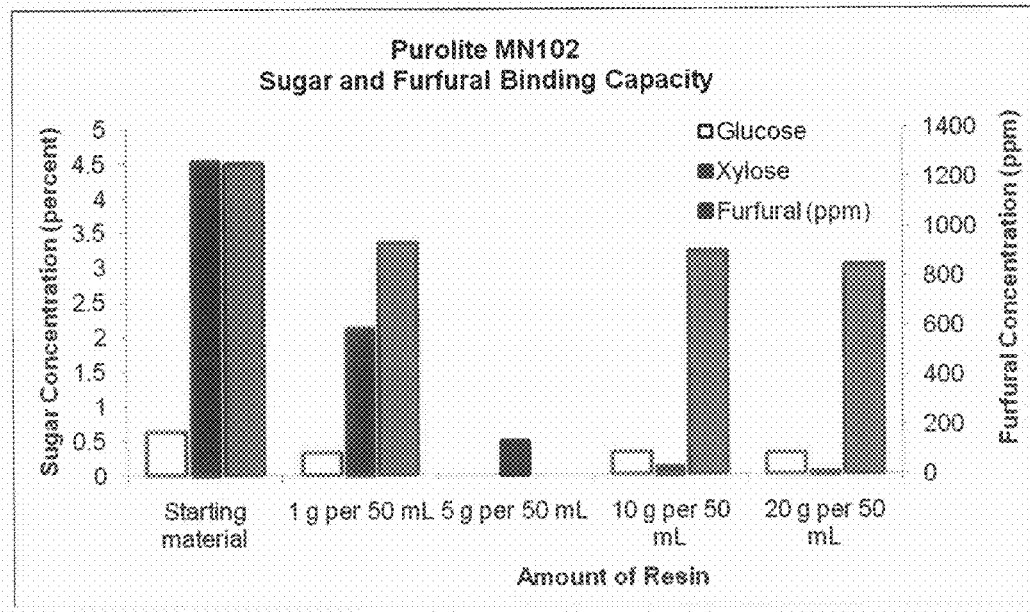
FIG. 13A is a graph of the sugar (glucose and xylose) concentration and furfural binding capacity of the Purolite® MN102 for the liquid component (starting material) and at various amounts of resin.

TABLE 6A presents the sugar (glucose and xylose) concentration and furfural binding capacity of the Dowex® Optipose L493 resin for the liquid component (starting material) and at various amounts of resin as illustrated in FIG. 13A.

TABLE 6B presents the ion exchange system resin bed configuration according to Example 2.

TABLE 6C presents the composition of the filtered liquid component supplied to the system and the composition of the samples of treated liquid component eluted from the system according to Example 2.

TABLE 7A presents the sugar (glucose and xylose) concentration and furfural binding capacity of the Purolite® MN102 resin for the liquid component (starting material) and at various amounts of resin as illustrated in FIG. 13A.

TABLE 7B presents the ion exchange system resin bed configuration according to Example 3.

TABLE 7C presents the composition of the filtered liquid component supplied to the system and the composition of the samples of treated liquid component eluted from the system according to Example 3.

DETAILED DESCRIPTION

Figure 1A:
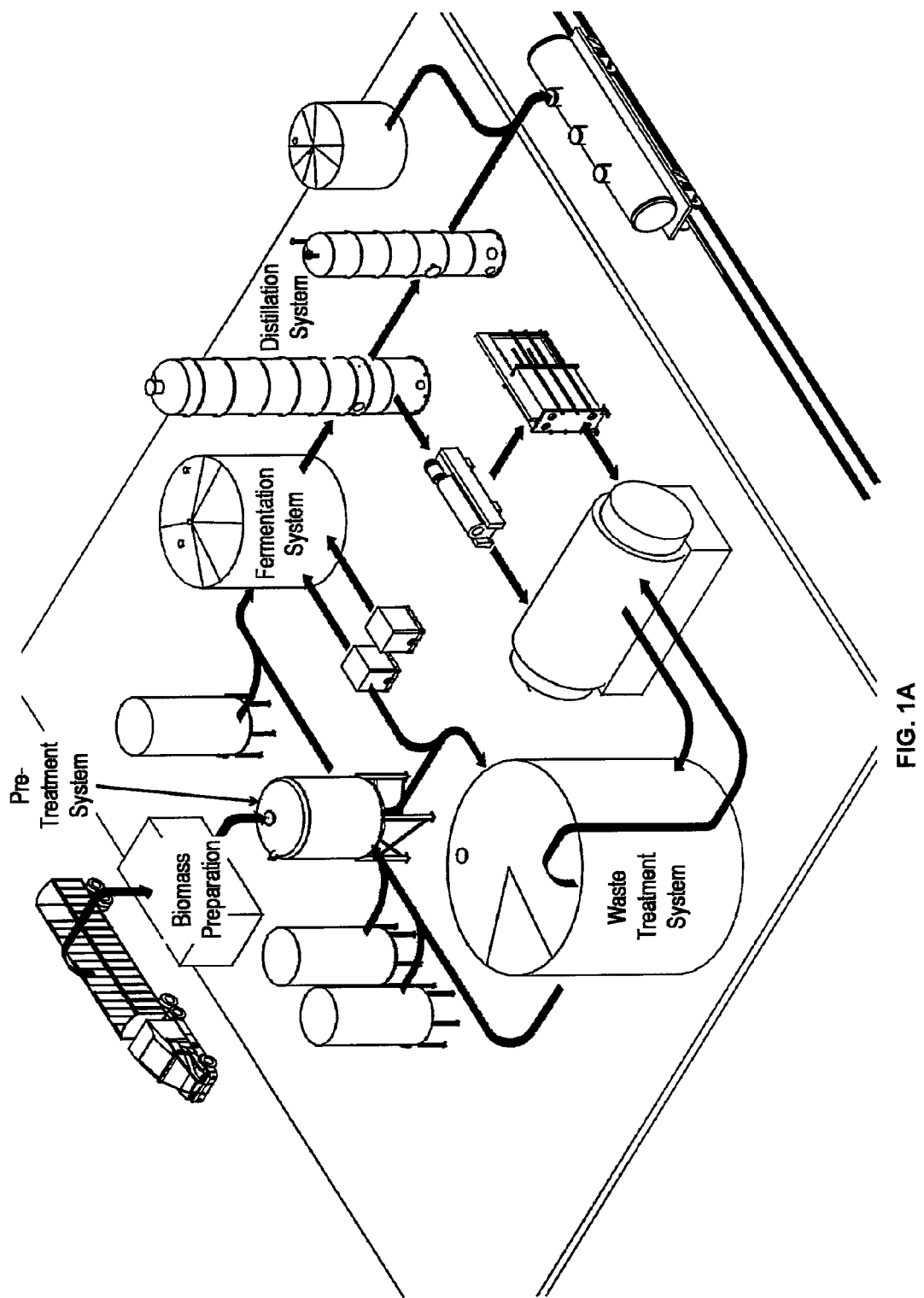
FIG. 1A is a perspective view of a biorefinery comprising a cellulosic ethanol production facility.

Referring to FIG. 1A, a biorefinery configured to produce ethanol from biomass is shown.

According to an exemplary embodiment, the biorefinery is configured to produce ethanol from biomass in the form of a lignocellulosic feedstock such as plant material from the corn plant (e.g. corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1A, the biorefinery comprises an area where biomass is delivered and prepared to be supplied to the cellulosic ethanol production facility. The cellulosic ethanol production facility comprises apparatus for preparation, pretreatment and treatment of the biomass into treated biomass suitable for fermentation into fermentation product in a fermentation system. The facility comprises a distillation system in which the fermentation product is distilled and dehydrated into ethanol. As shown in FIG. 1A, the biorefinery may also comprise a waste treatment system (shown as comprising an anaerobic digester and a generator). According to other alternative embodiments, the waste treatment system may comprise other equipment configured to treat, process and recover components from the cellulosic ethanol production process, such as a solid/waste fuel boiler, anaerobic digester, aerobic digester or other biochemical or chemical reactors.

Figure 1B:
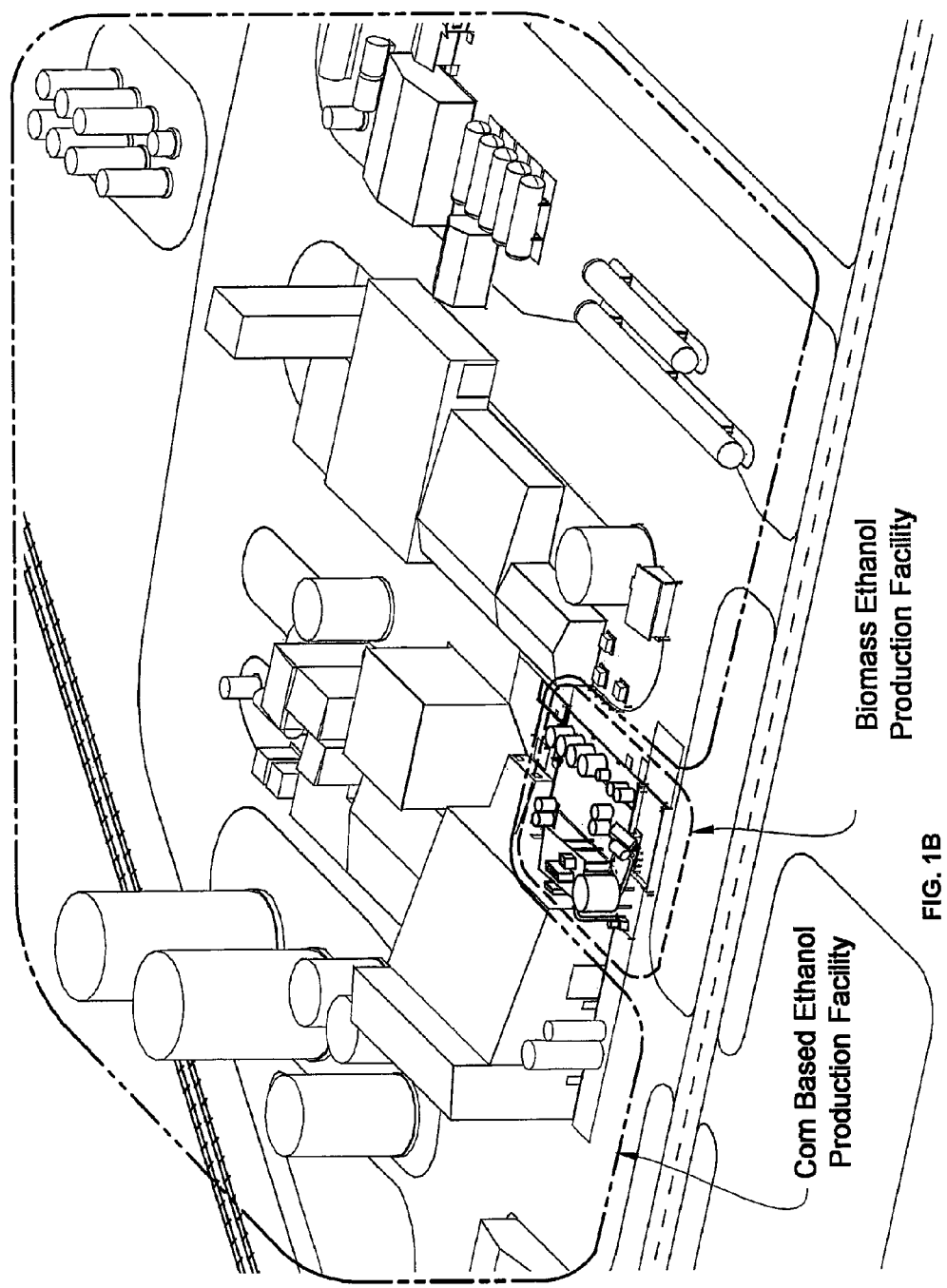
FIG. 1B is a perspective view of a biorefinery comprising a cellulosic ethanol production facility and a corn-based ethanol production facility.

As shown in FIG. 1B, according to an exemplary embodiment, a biorefinery may comprise a cellulosic ethanol production facility (which produces ethanol from lignocellulosic material and components of the corn plant) co-located with a corn-based ethanol production facility (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant or a facility that processes agricultural products.

Figure 2:
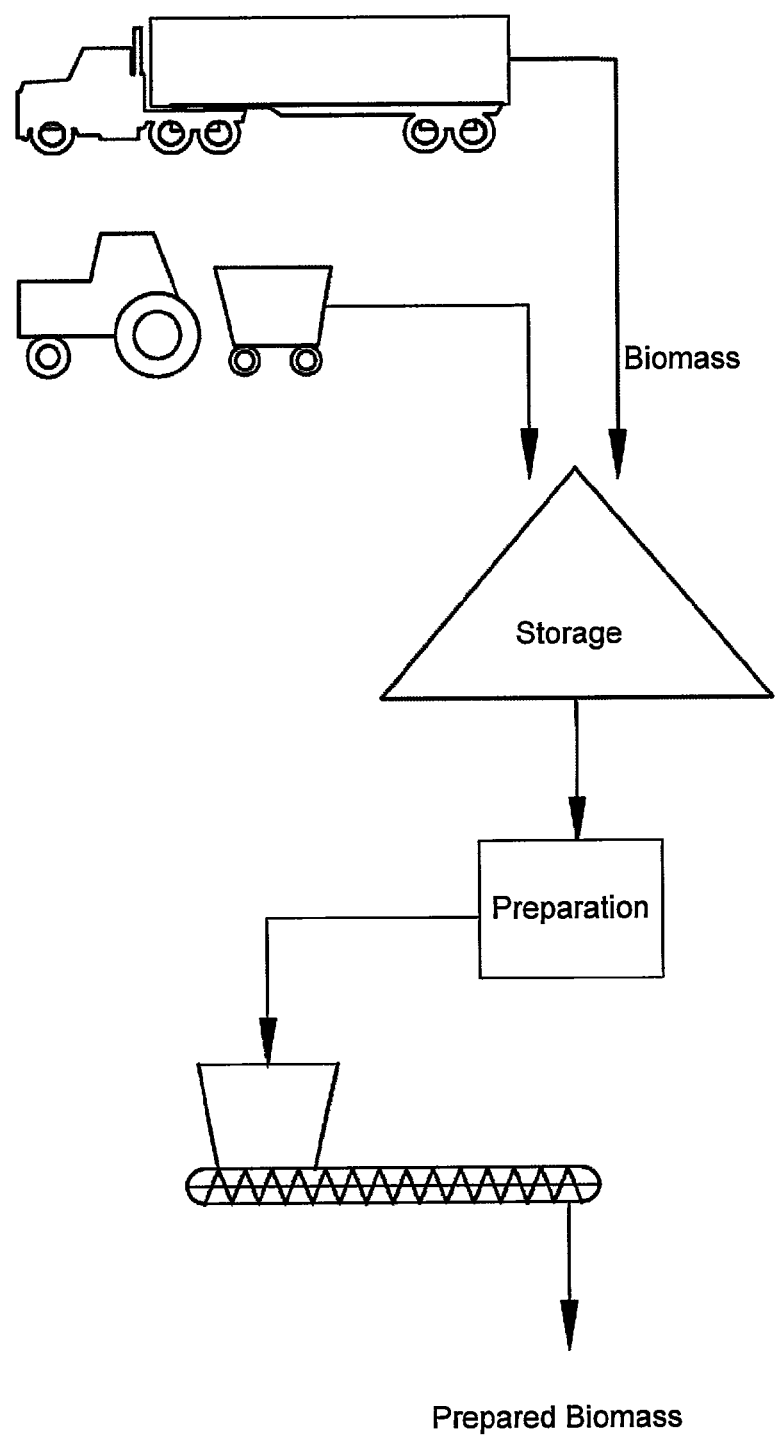
FIG. 2 is a schematic diagram of a system for receipt and preparation of biomass for a cellulosic ethanol production facility.

Referring to FIG. 2, a system for preparation of biomass delivered to the biorefinery is shown. The biomass preparation system may comprise apparatus for receipt/unloading of the biomass, cleaning (i.e. removal of foreign matter), grinding (i.e. milling, reduction or densification), and transport and conveyance for processing at the plant. According to an exemplary embodiment, biomass in the form of corn cobs and stover may be delivered to the biorefinery and stored (e.g. in bales, piles or bins, etc.) and managed for use at the facility. According to a preferred embodiment, the biomass may comprise at least 20 to 30 percent corn cobs (by weight) with corn stover and other matter. According to other exemplary embodiments, the preparation system of the biorefinery may be configured to prepare any of a wide variety of types of biomass (i.e. plant material) for treatment and processing into ethanol and other bioproducts at the plant.

Figure 3:
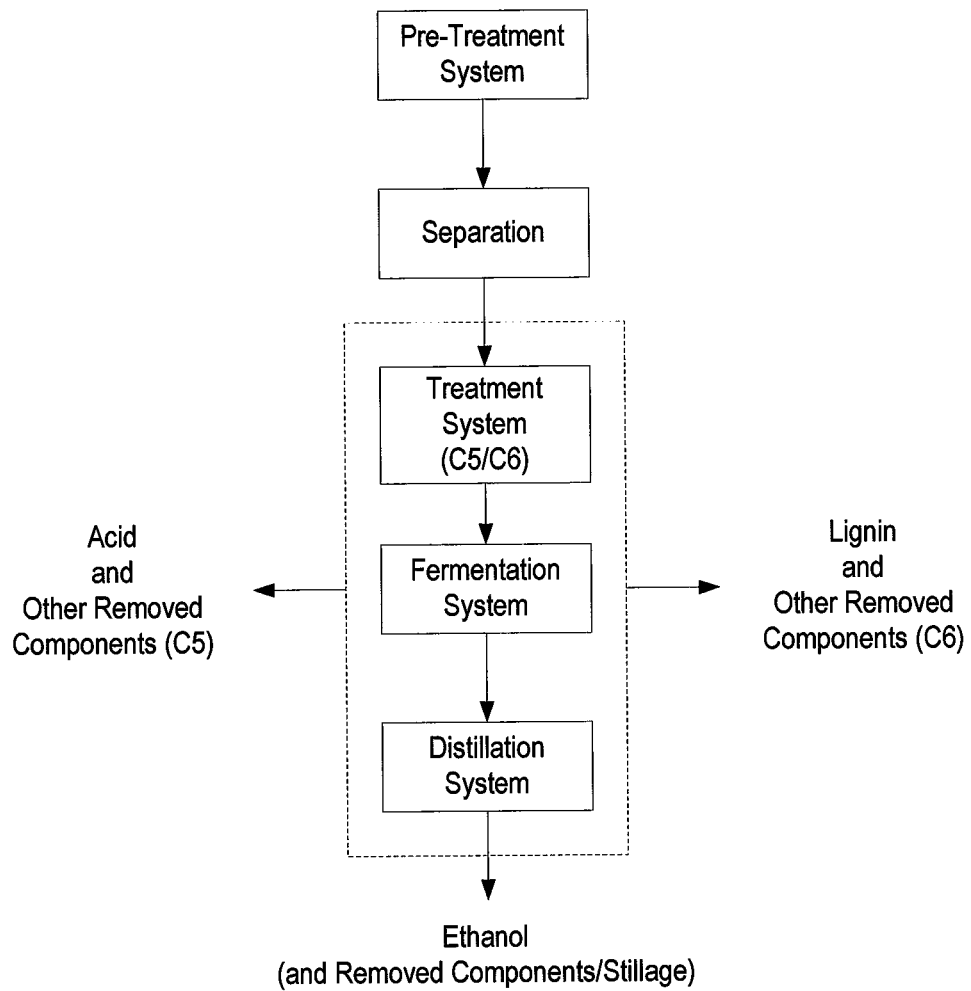
FIG. 3 is a schematic block diagram of a system for the production of ethanol from biomass.

Referring to FIG. 3, a schematic diagram of the cellulosic ethanol production facility is shown. According to a preferred embodiment, biomass comprising plant material from the corn plant is prepared and cleaned at a preparation system. After preparation, the biomass is mixed with water into a slurry and is pre-treated at a pre-treatment system. In the pre-treatment system, the biomass is broken down (e.g. by hydrolysis) to facilitate separation into a liquid component (e.g. a stream comprising the C5 sugars) and a solids component (e.g. a stream comprising cellulose from which the C6 sugars can be made available). The C5-sugar-containing liquid component (C5 stream) and C6-sugar-containing solids component (C6 stream) can be treated (as may be suitable) and fermented in a fermentation system. Fermentation product from the fermentation system is supplied to a distillation system where the ethanol is recovered.

As shown in FIGS. 3 and 4A, removed components from treatment of the C5 stream can be treated or processed to recover by-products, such as organic acids and furfural. As shown in FIGS. 3 and 4B, removed components from treatment of the C6 stream, such as lignin or other components, can be treated or processed into bioproducts or into fuel (such as lignin for a solid fuel boiler or methane produced by treatment of residual/removed matter such as acids and lignin in an anaerobic digester). As shown in FIGS. 4A, 4B and 4C, components removed during treatment and production of ethanol from the biomass from either or both the C5 stream and the C6 stream (or at distillation) may be processed into bioproducts (e.g. by-products or co-products) or recovered for use or reuse. As shown in FIG. 4C, removed components from the distillation system (such as stillage or removed solids) or from the treatment of the fermentation product before distillation (e.g. removed solids and particulate matter, which may comprise residual lignin, etc.) can be treated or processed into bioproducts or fuel (e.g. methane produced in an anaerobic digester).

According to a preferred embodiment, the biomass comprises plant material from the corn plant, such as corn cobs, husks and leaves and stalks; the composition of the plant material (i.e. cellulose, hemicellulose and lignin) will be approximately as indicated in TABLES 1A and 1B. According to a preferred embodiment, the plant material comprises corn cobs, husks/leaves and stalks (i.e. after cleaning/removal of foreign matter); for example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any other combinations of cobs, husks/leaves and stalks from the corn plant. See TABLE 1A. According to an exemplary embodiment, corn stalks comprise the upper half or three-quarters portion of the stalk. According to an alternative embodiment, the lignocellulosic plant material may comprise fiber from the corn kernel (e.g. in some combination with other plant material). TABLE 1B provides typical and expected ranges believed to be representative of the composition of biomass comprising lignocellulosic material from the corn plant. According to exemplary embodiments, the lignocellulosic plant material of the biomass (from the corn plant) will comprise (by weight) cellulose at about 30 to 55 percent, hemicellulose at about 20 to 50 percent, and lignin at about 10 to 25 percent; according to a particularly preferred embodiment, the lignocellulosic plant material of the biomass (cobs, husks/leaves and stalk portions from the corn plant) will comprise (by weight) cellulose at about 35 to 45 percent, hemicellulose at about 24 to 42 percent, and lignin at about 12 to 20 percent. According to a particularly preferred embodiment, pre-treatment of the biomass will yield a liquid component that comprises (by weight) xylose at no less than 1.0 percent and a solids component that comprises (by weight) cellulose (from which glucose can be made available) at no less than 45 percent.

Figure 5A:
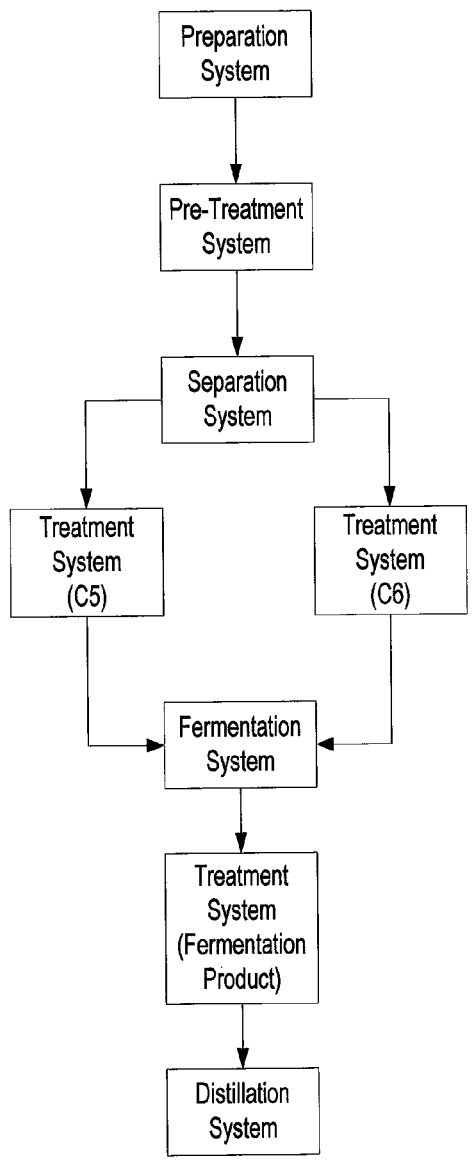
FIGS. 5A and 5B are schematic diagrams of the process flow for systems for the production of ethanol from biomass.
Figure 5B:
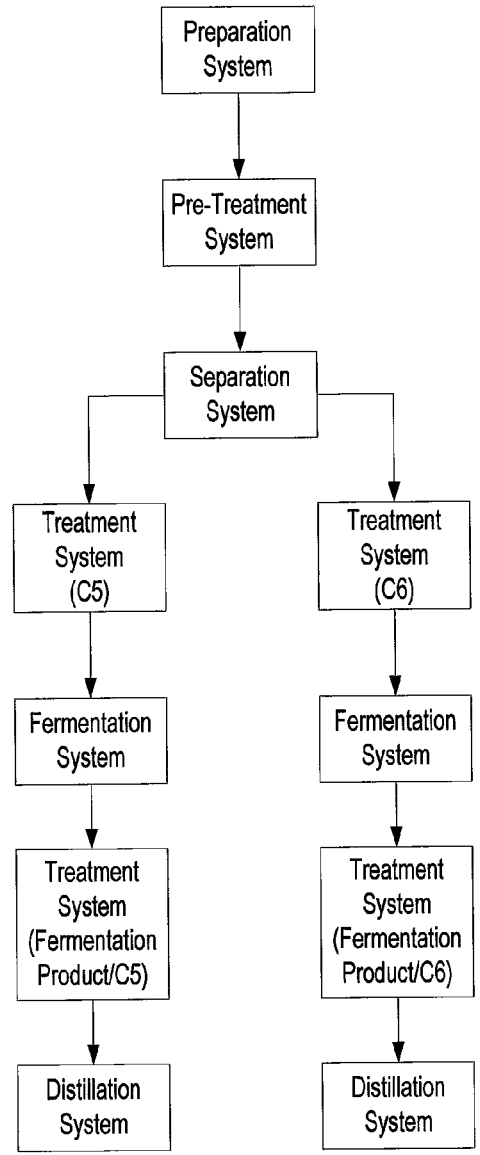

Referring to FIGS. 5A and 5B, exemplary embodiments of systems for the production of ethanol from biomass are shown. As shown in FIGS. 5A and 5B, biomass is pre-treated in a pre-treatment system and then separated into a liquid component and a solids component.

According to a preferred embodiment, in the pre-treatment system an acid will be applied to the prepared biomass to facilitate the break down of the biomass for separation into the liquid component (C5 stream from which fermentable C5 sugars can be recovered) and the solids component (C6 stream from which fermentable C6 sugars can be accessed). According to a preferred embodiment, the acid can be applied to the biomass in a reaction vessel under determined operating conditions (i.e. acid concentration, pH, temperature, time, pressure, solids loading, flow rate, supply of process water or steam, etc.) and the biomass can be agitated/mixed in the reaction vessel to facilitate the break down of the biomass. According to exemplary embodiments, an acid such as sulfuric acid, hydrochloric acid, nitric acid, phosphoric acid, acetic acid, etc. (or a formulation/mixture of acids) can be applied to the biomass. According to a particularly preferred embodiment, sulfuric acid will be applied to the biomass in pre-treatment.

The liquid component (C5 stream) comprises water, dissolved sugars (such as xylose, arabinose and glucose) to be made available for fermentation into ethanol, acids and other soluble components recovered from the hemicellulose. (TABLE 2B provides typical and expected ranges believed to be representative of the composition of biomass comprising lignocellulosic material from the corn plant.) According to an exemplary embodiment, the liquid component may comprise approximately 5 to 7 percent solids (i.e. suspended/residual solids such as partially-hydrolyzed hemicellulose, cellulose and lignin). According to a particularly preferred embodiment, the liquid component will comprise at least 2 to 4 percent xylose (by weight); according to other exemplary embodiments, the liquid component will comprise no less than 1 to 2 percent xylose (by weight). TABLES 2A and 2B list the composition of the liquid component of pre-treated biomass (from prepared biomass as indicated in TABLES 1A and 1B) according to exemplary and representative embodiments.

The solids component (C6 stream) comprises water, acids and solids such as cellulose from which sugar, such as glucose, can be made available for fermentation into ethanol, and lignin. (TABLE 3B provides typical and expected ranges believed to be representative of the composition of biomass comprising lignocellulosic material from the corn plant.) According to an exemplary embodiment, the solids component may comprise approximately 10 to 40 percent solids (by weight) (after separation); according to a particularly preferred embodiment, the solids component will comprise approximately 20 to 30 percent solids (by weight). According to a preferred embodiment, the solids in the solids component comprise no less than 30 percent cellulose and the solids component may also comprise other dissolved sugars (e.g. glucose and xylose). TABLES 3A and 3B list the composition of the solids component of pre-treated biomass (from prepared biomass as indicated in TABLES 1A and 1B) according to exemplary and representative embodiments.

During pre-treatment, the severity of operating conditions (such as pH, temperature and time) may cause formation of components that are inhibitory to fermentation. For example, under some conditions, the dehydration of C5 sugars (such as xylose or arabinose) may cause the formation of furfural and/or hydroxymethylfurfural (HMF). Acetic acid may also be formed, for example when acetate is released during the break down of cellulose in pre-treatment. Sulfuric acid, which may be added to prepared biomass to facilitate pre-treatment, if not removed or neutralized, may also be inhibitory to fermentation. According to an exemplary embodiment, by adjusting pre-treatment conditions (such as pH, temperature and time), the formation of inhibitors can be reduced or managed; according to other exemplary embodiments, components of the pre-treated biomass may be given further treatment to remove or reduce the level of inhibitors (or other undesirable matter).

Referring to FIGS. 5A and 5B, after pre-treatment and separation the C5 stream and the C6 stream are processed separately; as shown, the C5 stream and the C6 stream may be processed separately prior to co-fermentation (C5/C6 fermentation as shown in FIG. 5A) or processed separately including separate fermentation (separate C5 fermentation and C6 fermentation as shown in FIG. 5B).

Treatment of the C5 stream (liquid component) of the biomass may be performed in an effort to remove components that are inhibitory to efficient fermentation (e.g. furfural, HMF, sulfuric acid and acetic acid) and residual lignin (or other matter) that may not be fermentable from the C5 sugar component so that the sugars (e.g. xylose, arabinose, as well as other sugars such as glucose) are available for fermentation. The C5 sugars in the C5 stream may also be concentrated to improve the efficiency of fermentation (e.g. to improve the titer of ethanol for distillation).

Treatment of the C6 stream (solids component) of the biomass may be performed to make the C6 sugars available for fermentation. According to a preferred embodiment, hydrolysis (such as enzyme hydrolysis) may be performed to access the C6 sugars in the cellulose; treatment may also be performed in an effort to remove lignin and other non-fermentable components in the C6 stream (or to remove components such as residual acid or acids that may be inhibitory to efficient fermentation).

According to an exemplary embodiment shown in FIG. 5A, after pre-treatment and separation the C5 stream and the C6 stream can be treated separately and subsequently combined after treatment (e.g. as a slurry) for co-fermentation in the fermentation system to produce a C5/C6 fermentation product from the available sugars (e.g. xylose and glucose); the C5/C6 fermentation product can (after treatment, if any) be supplied to the distillation system for recovery of the ethanol (e.g. through distillation and dehydration). According to an exemplary embodiment shown in FIG. 5B, the C5 stream and the C6 stream can each be separately processed through fermentation and distillation (after treatment, if any) to produce ethanol. According to any preferred embodiment, a suitable fermenting organism (ethanologen) will be used in the fermentation system; the selection of an ethanologen may be based on various considerations, such as the predominant types of sugars present in the slurry. Dehydration and/or denaturing of the ethanol produced from the C5 stream and the C6 stream may be performed either separately or in combination.

Figure 6A:
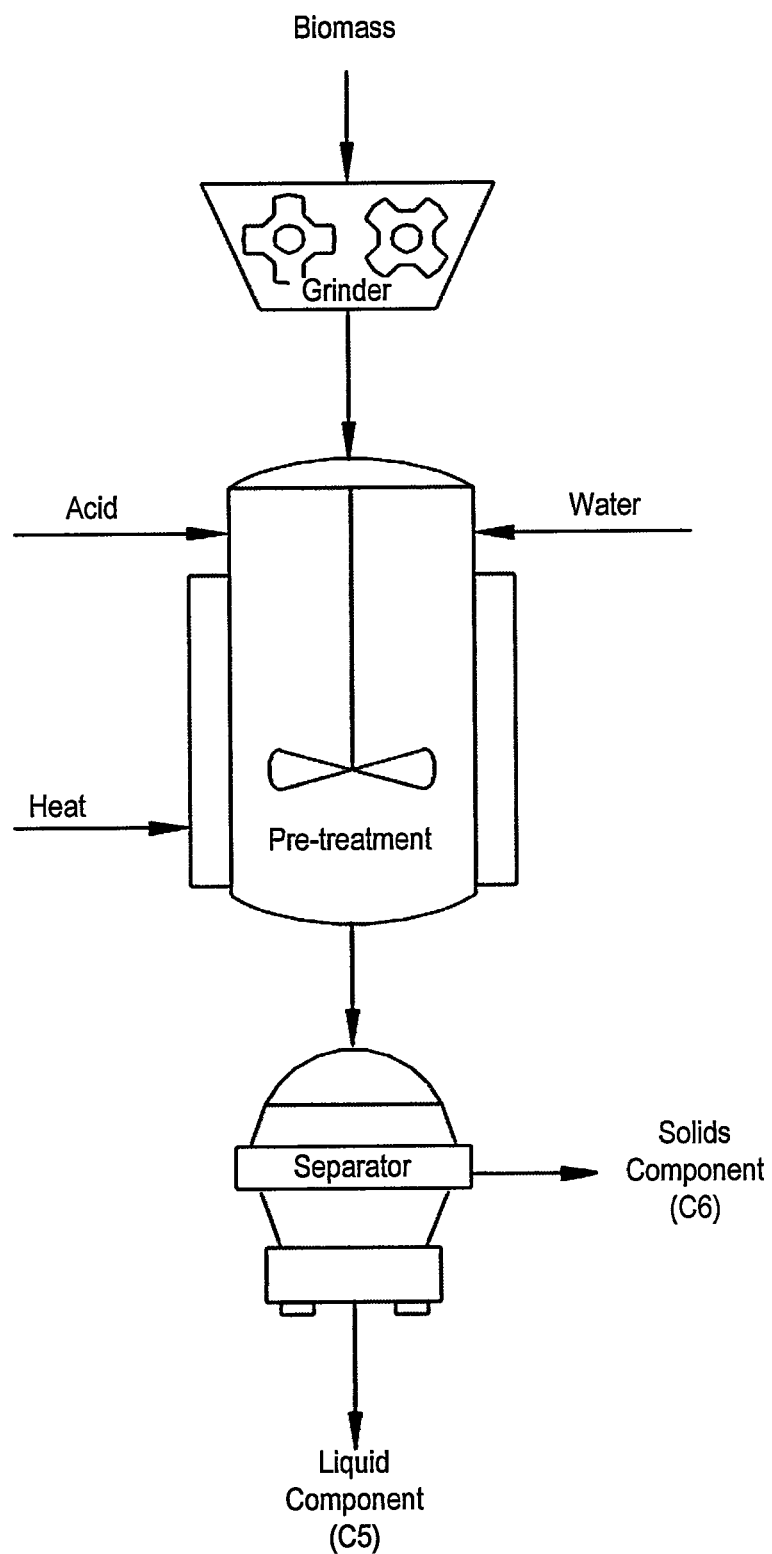
FIG. 6A is a schematic block diagram of apparatus used for preparation, pre-treatment and separation of biomass.
Figure 6B:
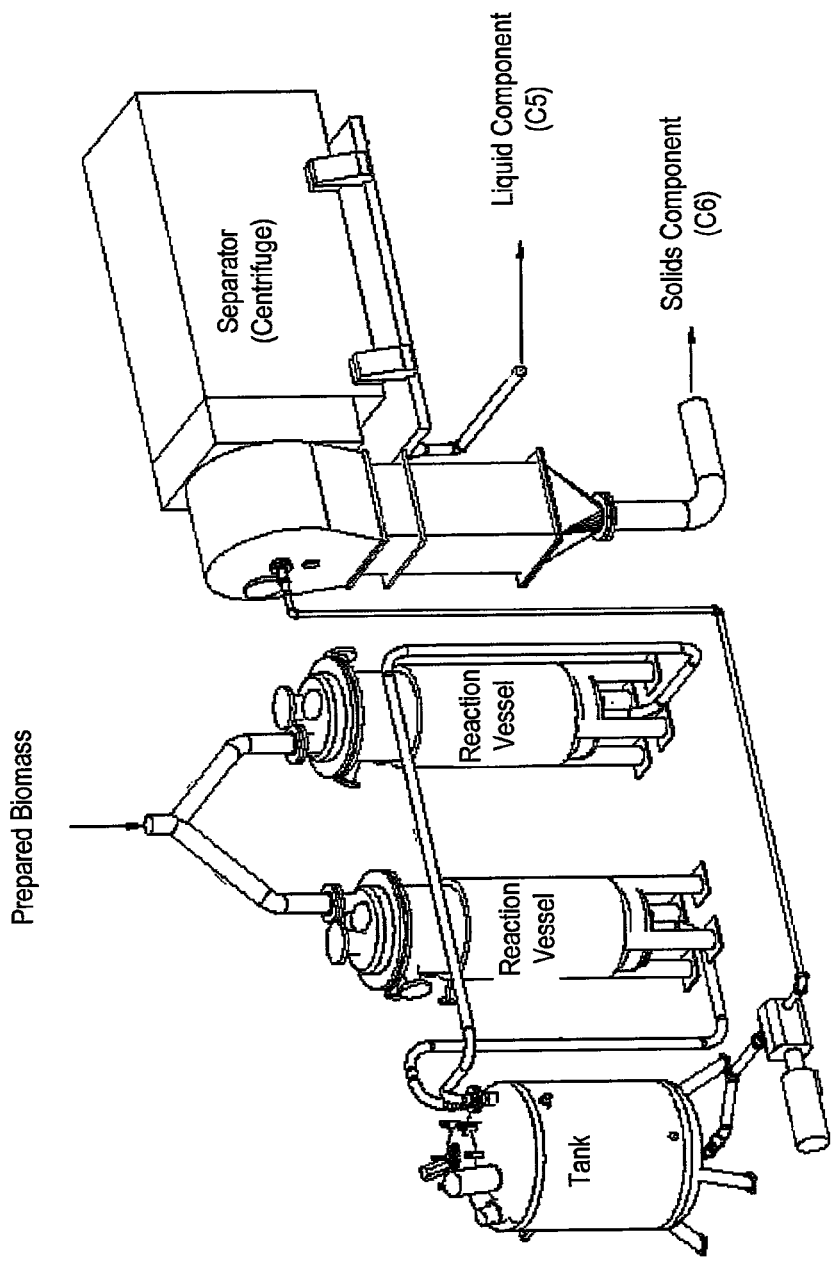
FIG. 6B is a perspective view of apparatus used to pre-treat and separate the biomass.
Figure 7:
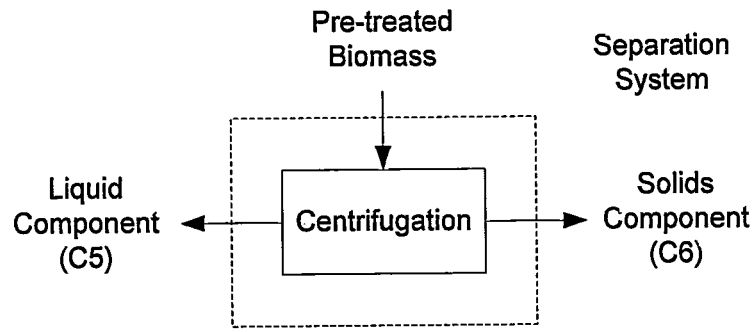
FIG. 7 is a schematic diagram of the process flow for separation of pre-treated biomass into a liquid component and a solids component.

FIGS. 6A and 6B show the apparatus used for preparation, pre-treatment and separation of lignocellulosic biomass according to an exemplary embodiment. As shown, biomass is prepared in a grinder (e.g. grinder mill). Pre-treatment of the prepared biomass is performed in a reaction vessel (or set of reaction vessels) supplied with prepared biomass and acid/water in a predetermined concentration (or pH) and other operating conditions. As shown in FIGS. 6B and 7, the pre-treated biomass can be separated in a centrifuge into a liquid component (e.g. a C5 stream comprising primarily liquids with some solids and which may be referred to as "pentose liquor") and a solids component (e.g. a C6 stream comprising liquids and solids such as lignin and cellulose from which glucose can be made available by further treatment).

Figure 8A:
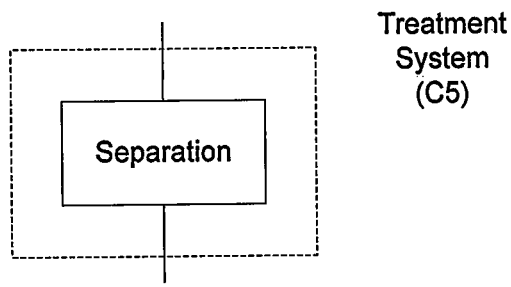
FIGS. 8A and 8B are schematic diagrams of a treatment system for the liquid component of pre-treated biomass.
Figure 8B:
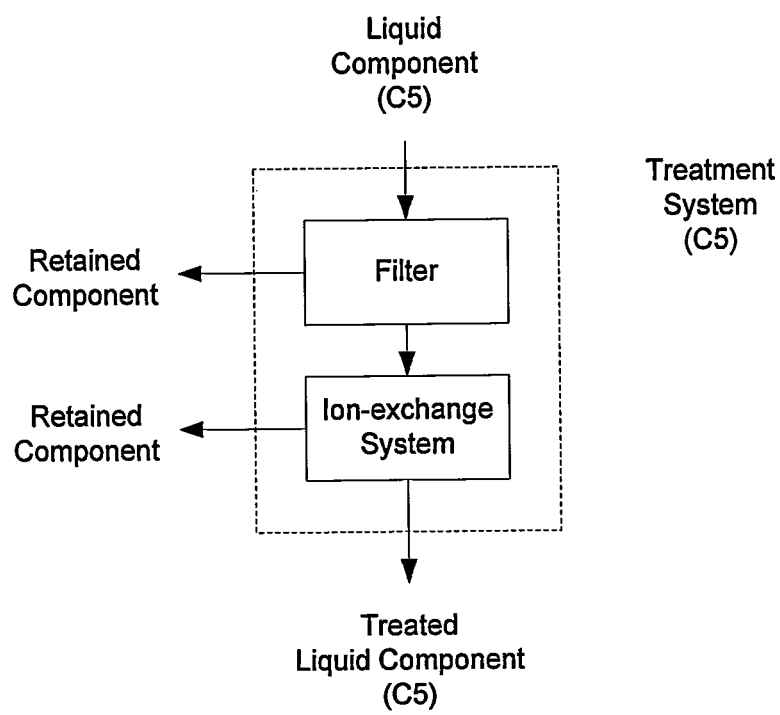

Referring to FIGS. 8A and 8B, a treatment system for the liquid component of the pre-treated biomass is shown. Treatment system comprises an apparatus for separating the liquid component into a treated liquid component and a retained component. According to any preferred embodiment, the treated liquid component comprises substantially the C5 sugars from the liquid component (C5 stream). The retained component comprises substantially any other constituents such as acid (e.g. sulfuric acid applied in pre-treatment and other acids that may be present in the C5 stream, such as acetic acid) and inhibitors that may be present (e.g. furfural and hydroxymethylfurfural that was produced or released into the C5 stream during pre-treatment).

Figure 9:
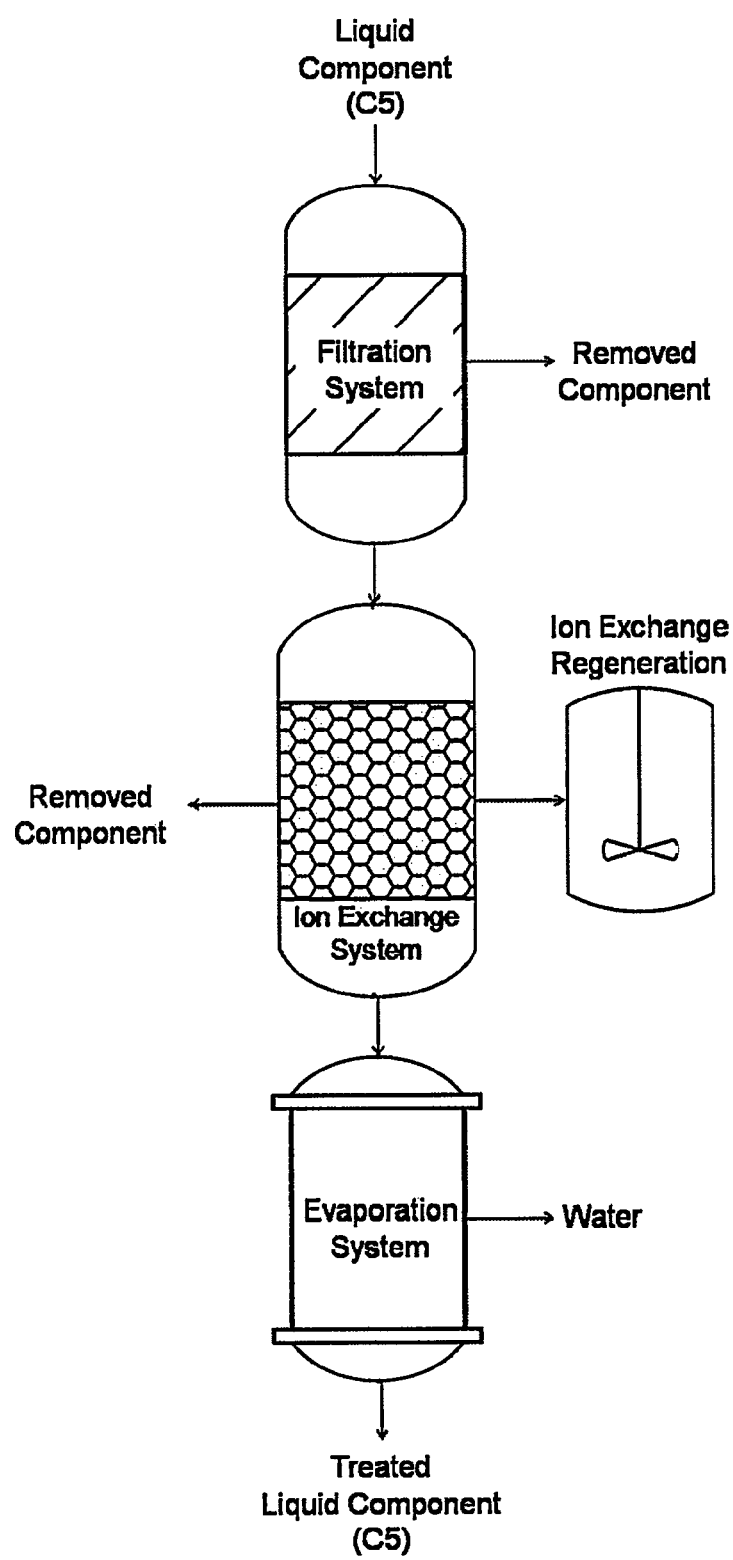
FIG. 9 is a schematic block diagram of an apparatus used to treat the liquid component of pre-treated biomass according to an exemplary embodiment.

As shown in FIGS. 8B and 9, according to a preferred embodiment, the treatment system comprises an initial stage filter and an ion exchange chromatography system. The initial stage filter comprises an inline filter (e.g. sock filter with 25-100 micron pore size) and is configured to separate and remove solids or particulate matter from the liquid component to yield a filtered liquid component. The filtered liquid component is then supplied to an ion exchange system. The ion exchange system is configured to separate and remove (e.g. as removed components or waste) inhibitors from the filtered liquid component to yield a treated liquid component comprising xylose and other soluble components not removed in the resin bed.

Figure 10:
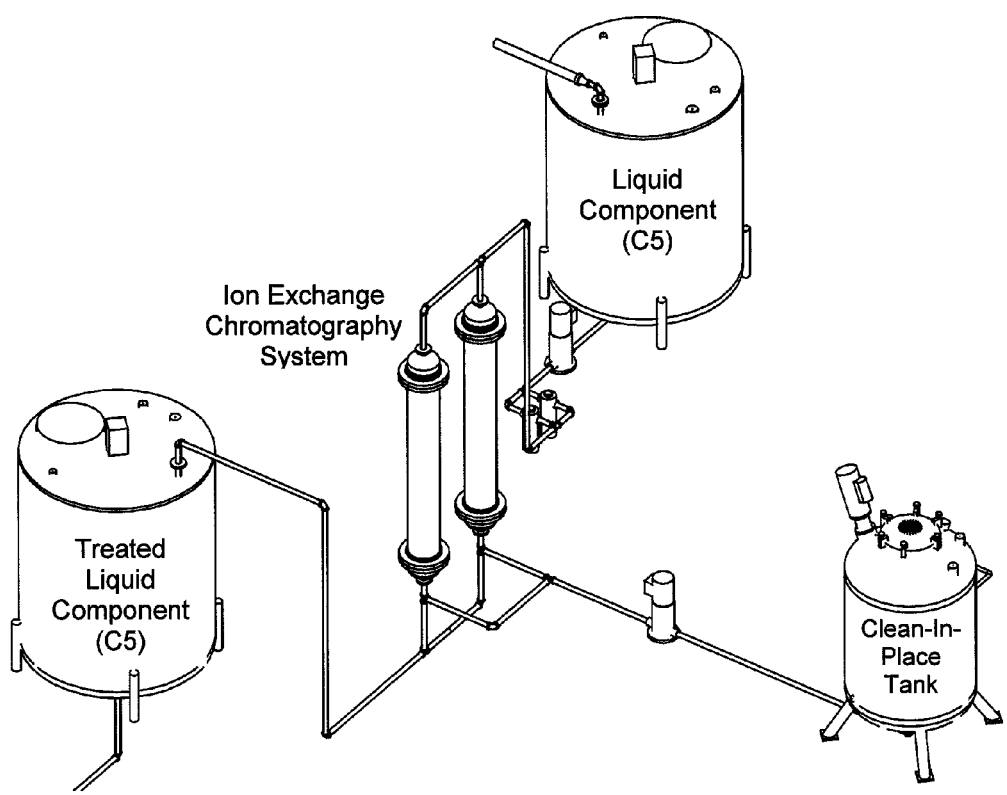
FIG. 10 is perspective view of a system used to treat the liquid component of pre-treated biomass according to an exemplary embodiment.

Referring to FIG. 10, a treatment system is shown according to an exemplary embodiment. The system comprises two ion exchange columns (configured in a parallel flow arrangement). Liquid component (C5 stream) is supplied (from a tank) through a pre-filter (e.g. 25 to 100 micron pore size to remove particulate matter) into the top of each column by a pump. Each column contains a bed that is configured to hold/retain a resin that is supplied to the column. The resin is selected to remove inhibitors (at least in some portion) under the operating conditions. Liquid component is eluted through the resin bed and exits at the bottom of the column as treated liquid component that is supplied to a tank. Each column in the system may selectively be used (i.e. one column used while the other column is being regenerated with fresh resin or cleaned, for example, by clean-in-place/caustic solution supplied from a tank). The treated liquid component can be supplied to the fermentation system.

According to a particularly preferred embodiment, the ion exchange system can be constructed from a tube of a suitable alloy (e.g. stainless steel) of a suitable size (e.g. 96 inches in height and 4 inches in diameter) filled with the appropriate resin. According to other embodiments, any ion exchange system (or ion exchange chromatography system) capable of being configured to treat the liquid component to remove inhibitors and yield C5 sugars for fermentation may be used or constructed.

According to an exemplary embodiment the resin will comprise weak base functional groups that are supported on porous resin beads. According to a preferred embodiment, the resin will be capable of adsorbing and reducing the level of inhibitors in the liquid component and can be regenerated with dilute acid or base and water. According to a particularly preferred embodiment the resin will be capable of adsorbing furfural and hydroxymethylfurfural, but will not adsorb substantial amounts of sugars (e.g. xylose and glucose).

A series of examples were conducted according to an exemplary embodiment of the system in an effort to evaluate the performance of the apparatus with various operating conditions and using different types of resin materials for the treatment of the liquid component (C5 stream) of the pre-treated biomass. Prepared biomass in the form of ground corn cobs (about 14.3 percent solids weight to weight) in a slurry with water was pre-treated in a reaction vessel with dilute sulfuric acid in a concentration of about 0.9 percent (weight to weight) at a temperature of about 150 degrees Celsius for a reaction time of about 10 minutes. The pre-treated biomass was cooled to about 80 degrees Celsius then separated by centrifuge into a liquid component (C5 stream) and a solids component (C6 stream). The liquid component was filtered using a 25 micron pore-size filter. The filtered liquid component (i.e. hydrolysate) was treated in the system as indicated in the examples.

EXAMPLE 1A

Figure 11A:
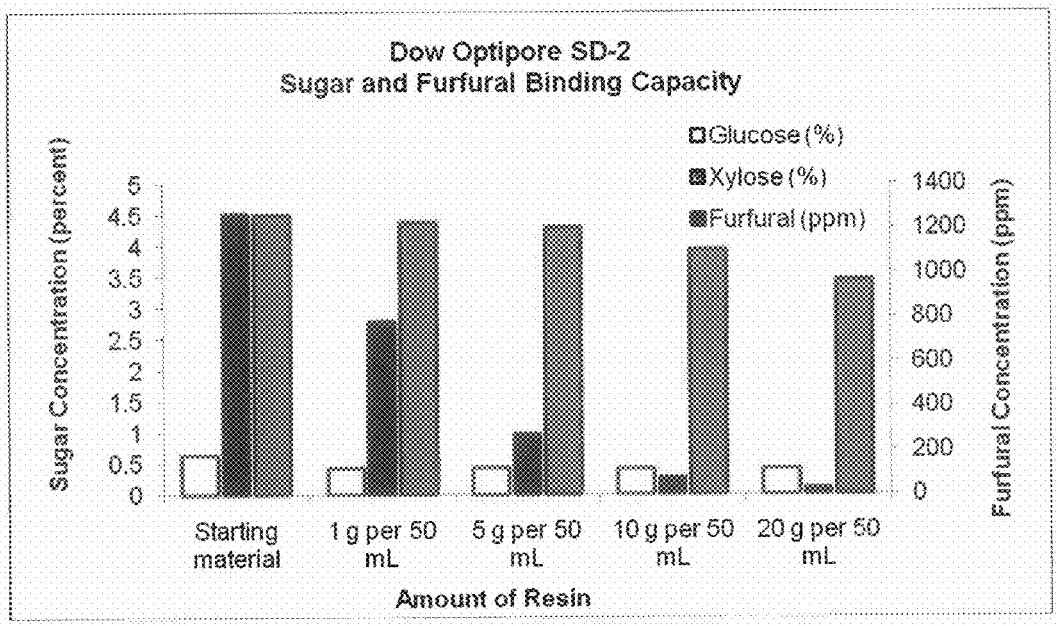
FIG. 11A is a bar graph of the sugar (glucose and xylose) concentration and furfural binding capacity of the Dow® Optipore® SD-2 for the liquid component (starting material) and at various amounts of resin.
Figure 11B:
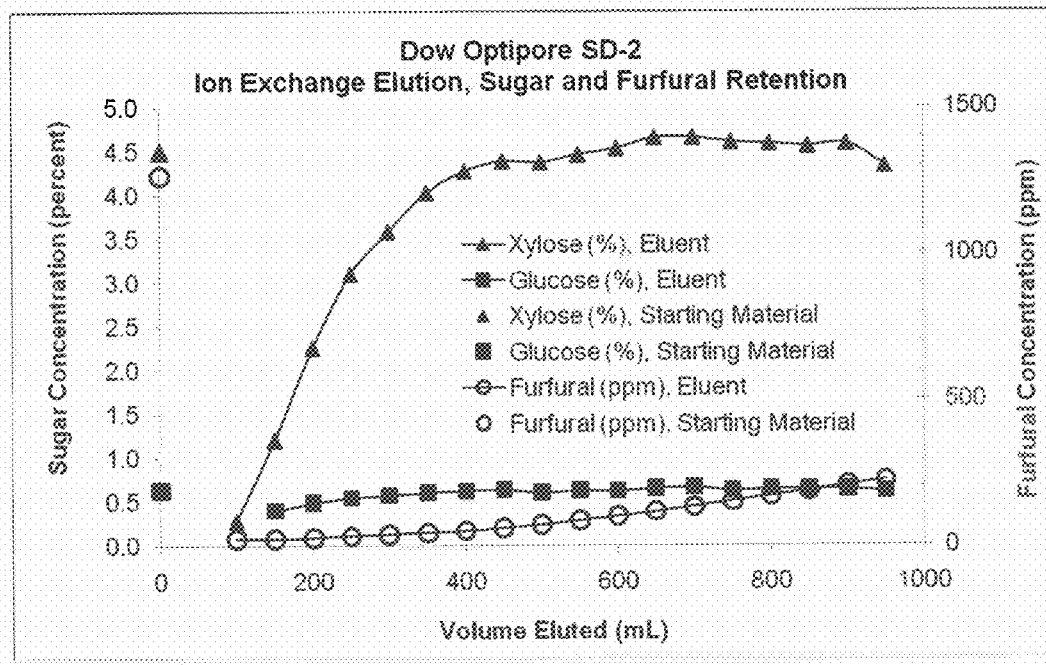
FIG. 11B is a graph of results obtained through the use of the treatment system according to Example 1A.

An ion exchange system was used in Example 1A to treat filtered liquid component (i.e. hydrolysate) using adsorbent macroporous styrene-divinylbenzene copolymer resin material comprising a tertiary amine functional group, dry weight capacity 0.8 milliequivalents per gram (meq/g), typical surface area 800 square meters per gram ($m^2/g$), and average pore diameter of 50 Angstroms (available under the trade name Optipore® SD-2 from Dow Chemical Co. of Midland, Mich.). The binding capacity of the Optipore® SD-2 resin material was evaluated with respect to xylose, glucose and furfural, as shown in FIG. 11A and TABLE 4. The Optipore® SD-2 resin material was then used in the resin bed of the ion exchange system, configured as indicated in TABLE 5A. The filtered liquid component from the pre-treated biomass was supplied to the system for treatment. The filtered liquid component (hydrolysate) was pumped through the resin bed at a rate of between about 37-43 milliliters per minute. The filtered liquid component was supplied at about pH 1.8. Samples of the treated liquid component eluted from the system were taken at regular intervals of cumulative volume flow. The composition of the filtered liquid component supplied to the system and of the samples of treated liquid component eluted from the system were analyzed for (among other things) xylose concentration, glucose concentration and furfural. It was observed that the ion exchange resin demonstrated efficacy in the removal of furfural from the liquid component. It was also observed that a suitable reduced level of furfural (i.e. to below about 500 ppm) was achieved without substantially affecting the levels of xylose or glucose (which were maintained at or near the starting level). The results are shown in TABLE 5B and FIG. 11B.

EXAMPLE 1B

Figure 11C:
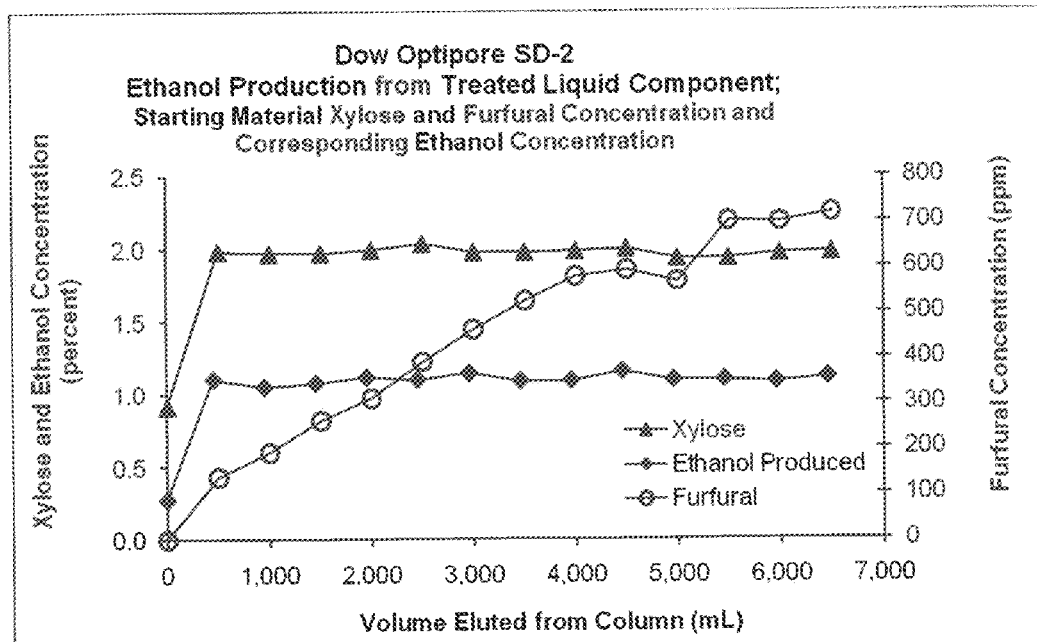
FIGS. 11C through 11E are graphs of results obtained through the use of the treatment system according to Example 1B.
Figure 11D:
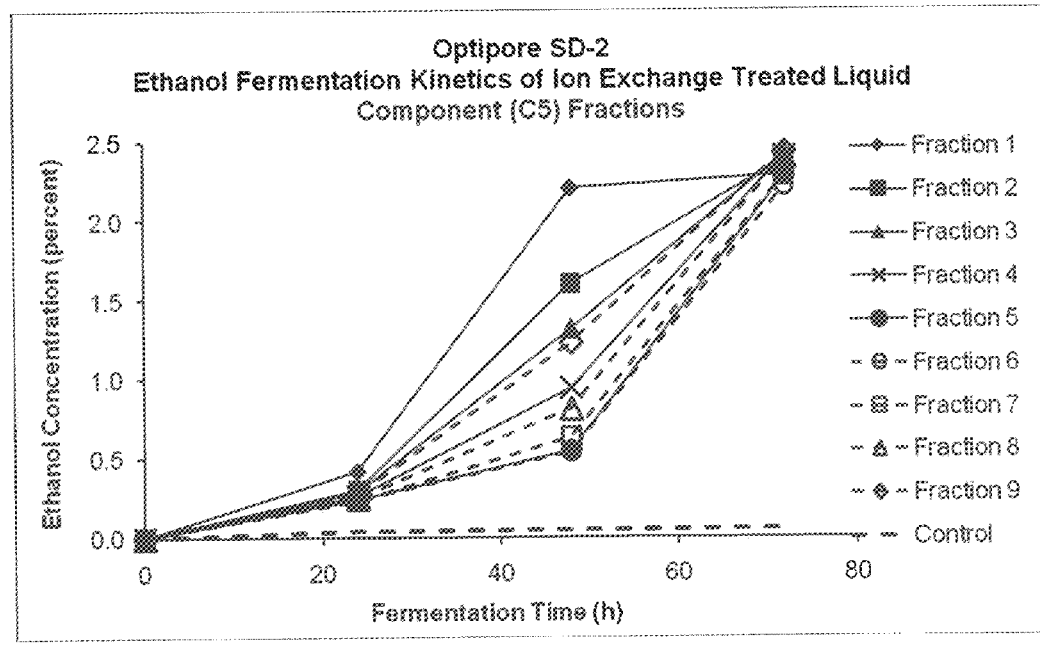
Figure 11E:
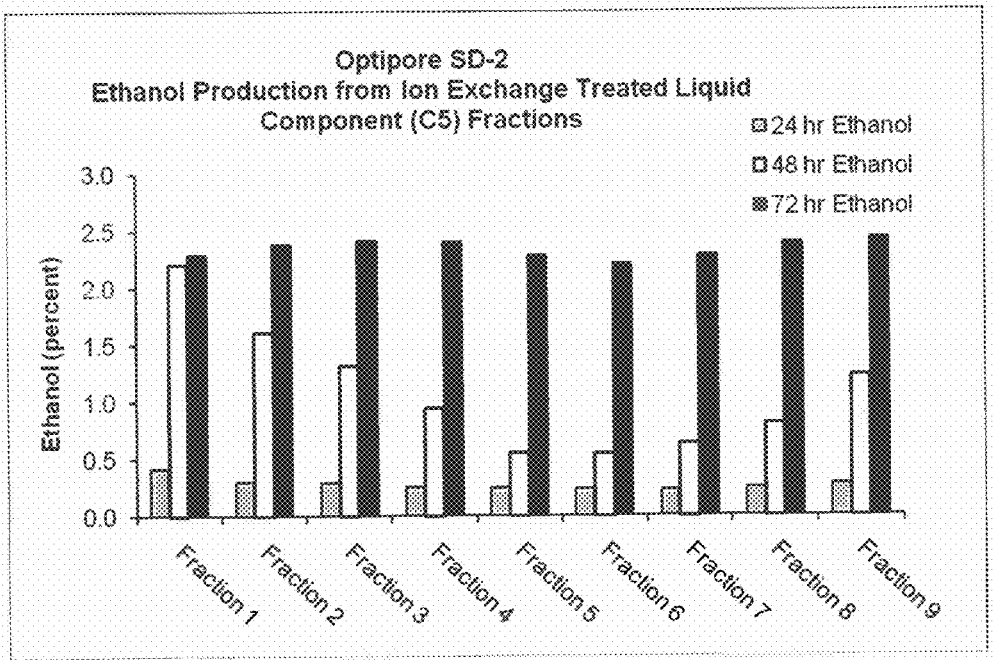

The ion exchange system as configured for Example 1A was used in Example 1B with Optipore® SD-2 resin material in the resin bed of the ion exchange system, configured as indicated in TABLE 5C. The filtered liquid component from the pre-treated biomass was supplied to the ion exchange system for treatment. The filtered liquid component (hydrolysate) was pumped through the resin bed at a rate of about 75 milliliters per minute. Samples of the treated liquid component eluted from the system were taken at regular intervals (e.g. fractions). Each fraction of treated liquid component was fermented into a fermentation product; the fermentation product was sampled at intervals of 24 hours, 48 hours and 72 hours (which was considered to be essentially completed fermentation). The samples of the treated liquid component and the fermentation product were analyzed. It was observed that the ion exchange system lowered the level of furfural in the liquid component to a level where it no longer was inhibitory to fermentation, and improved the yield of ethanol from the liquid component in fermentation (from effectively near zero to a level of approximately 2.4 percent). The results are shown in TABLES 5D and 5E and FIGS. 11C through 11E.

EXAMPLE 1C

Figure 11F:
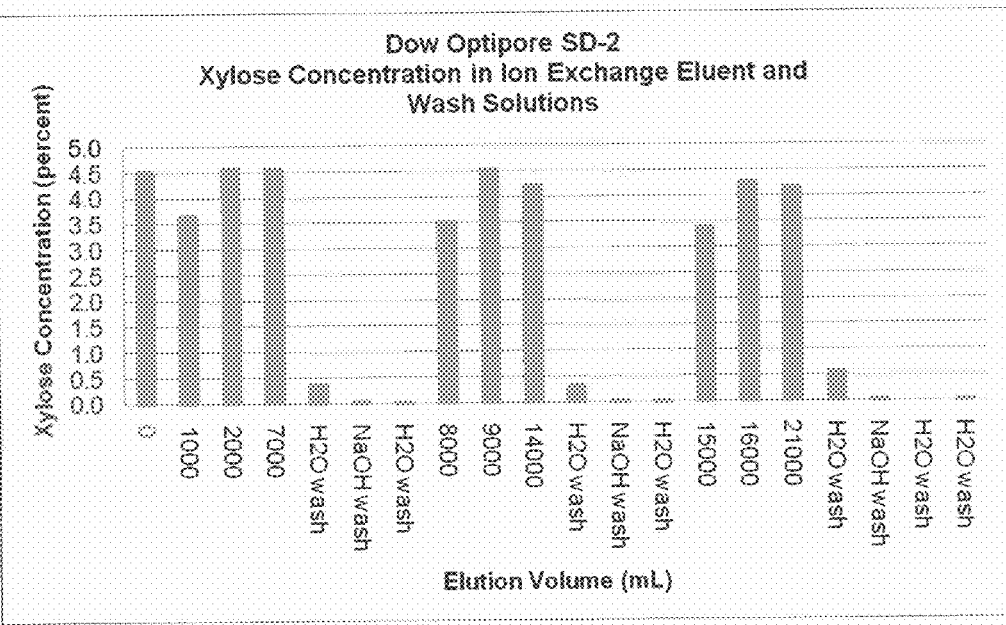
FIGS. 11F through 11G are graphs of results obtained through the use of the treatment system according to Example 1C.
Figure 11G:
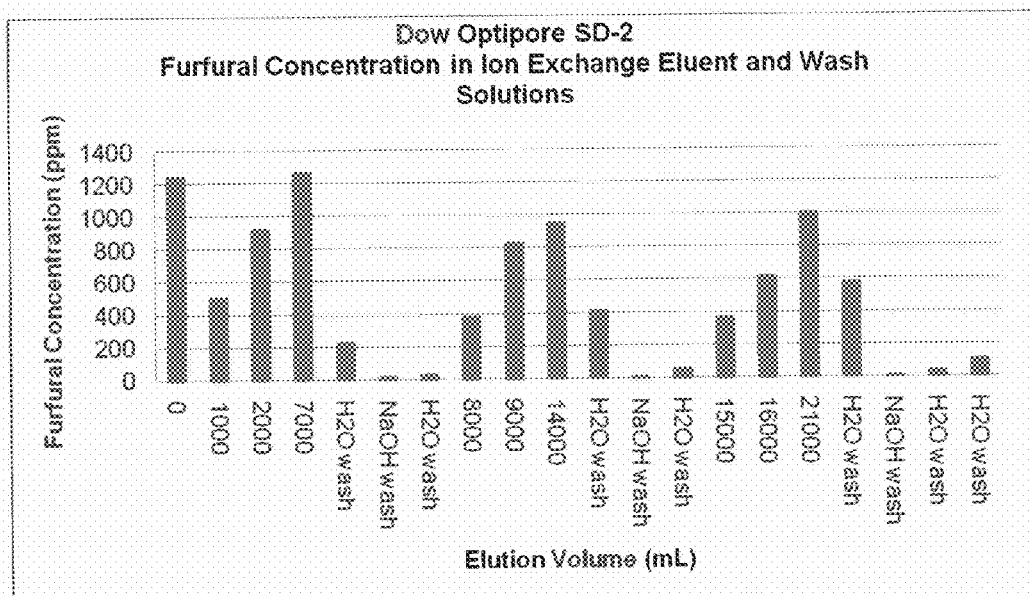

The ion exchange system as configured for Example 1A was used in Example 1C with Optipore® SD-2 resin material in the resin bed of the ion exchange system, configured as indicated in TABLE 5F. The filtered liquid component from the pre-treated biomass was supplied to the system for treatment. The filtered liquid component (hydrolysate) was pumped through the resin bed at a rate of about 75 milliliters per minute. The system was regenerated (i.e. washing of the resin bed with deionized water and a caustic cleaning solution in the form of sodium hydroxide in a concentration of about 1 percent by weight) at regular intervals. Samples of the treated liquid component eluted from the system were taken at regular intervals of cumulative volume flow including through regeneration. The effect of regeneration on xylose concentration and furfural concentration (among other things) in the treated liquid component was evaluated. It was observed that the functionality of the ion exchange resin could be sustained after regeneration; the resins would continue to elute suitable levels of xylose after regeneration for at least 3 cycles. The results are shown in TABLE 5G and FIGS. 11F and 11G.

EXAMPLE 2

Figure 12A:
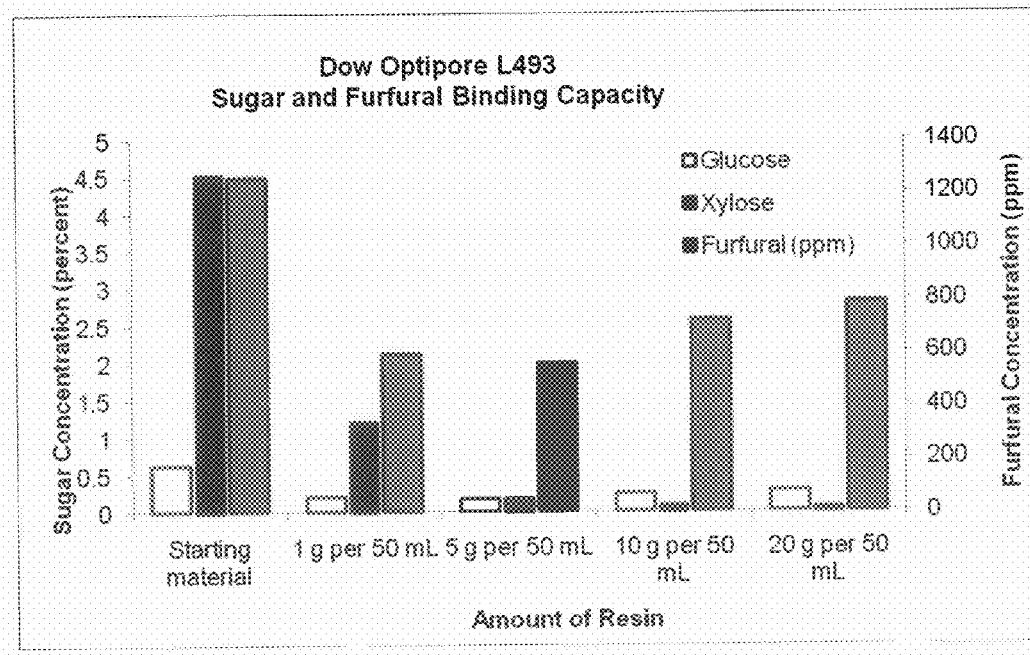
FIG. 12A is a graph of the sugar (glucose and xylose) concentration and furfural binding capacity of the Dow® Optipore® L493 for the liquid component (starting material) and at various amounts of resin.
Figure 12B:
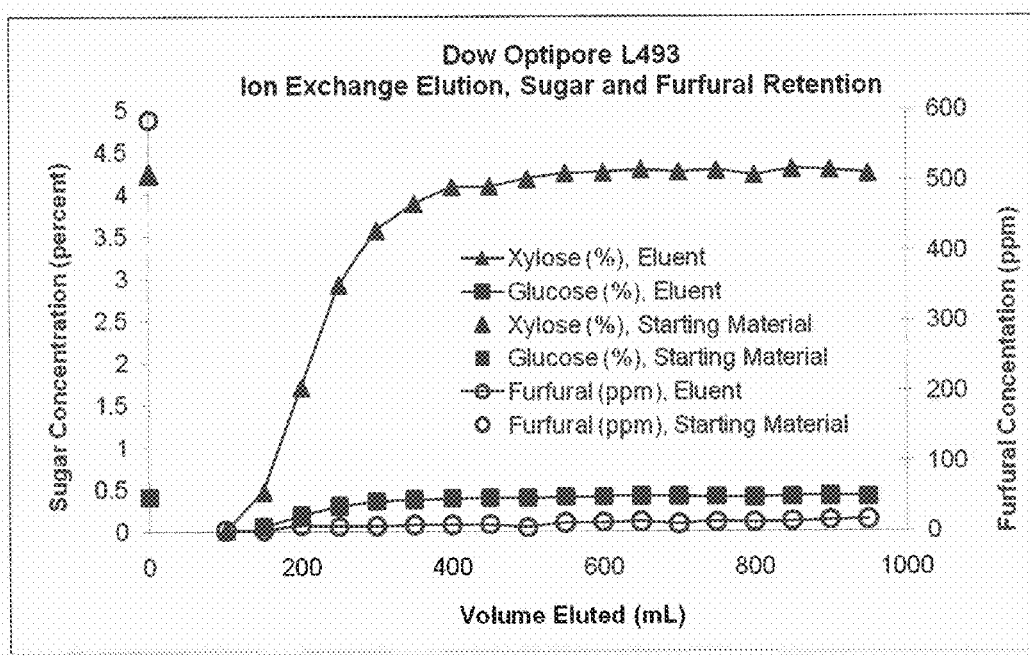
FIG. 12B is a graph of results obtained through the use of the treatment system according to Example 2.

The ion exchange system was used in Example 2 to treat filtered liquid component (i.e. hydrolysate) using macroporous styrenic polymer resin material comprising a hydrophobic adsorbent surface, BET surface area of 1100 m²/g, and average pore diameter of 46 Angstroms (available under the trade name Optipore® L493 from Dow Chemical Co. of Midland, Mich.). The binding capacity of the Optipore® L493 resin material was evaluated with respect to xylose, glucose and furfural, as shown in FIG. 12A and TABLE 6A. The Optipore® L493 resin material was then used in the resin bed of the ion exchange system, configured as indicated in TABLE 6B. The filtered liquid component from the pre-treated biomass was supplied to the system for treatment. The filtered liquid component (hydrolysate) was pumped through the resin bed at a rate of between about 40-50 milliliters per minute. The filtered liquid component was supplied at about pH 1.8. Samples of the treated liquid component eluted from the system were taken at regular intervals of cumulative volume flow. The composition of the filtered liquid component supplied to the system and of the samples of treated liquid component eluted from the system were analyzed for (among other things) xylose concentration, glucose concentration and furfural. It was observed that the resin retained furfural but did not retain xylose and glucose (which were eluted and comprised in the treated liquid component). The results are shown in TABLE 6C and FIG. 12B.

EXAMPLE 3

Figure 13B:
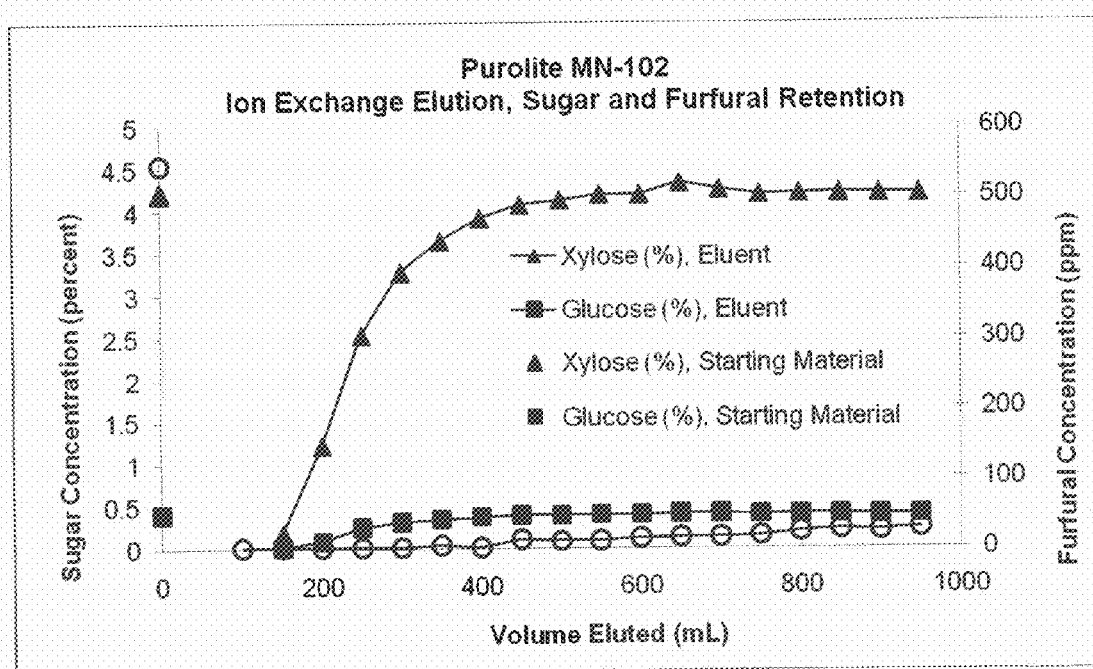
FIG. 13B is a graph of results obtained through the use of the treatment system according to Example 3.

The ion exchange system was used in Example 3 to treat filtered liquid component (i.e. hydrolysate) using crosslinked polystyrene resin material comprising a tert-amino functional group and surface area approximately 1000 m²/g (available under the trade name Purolite® MN-102 from Purolite Company of Bala Cynwyd, Pa.). The binding capacity of the Purolite® MN-102 resin material was evaluated with respect to xylose, glucose and furfural, as shown in FIG. 13A and TABLE 7A. The Purolite® MN-102 resin material was then used in the resin bed of the ion exchange system, configured as indicated in TABLE 7B. The filtered liquid component from the pre-treated biomass was supplied to the system for treatment. The filtered liquid component (hydrolysate) was pumped through the resin bed at a rate of between about 40-50 milliliters per minute. The filtered liquid component was supplied at about pH 1.8. Samples of the treated liquid component eluted from the system were taken at regular intervals of cumulative volume flow. The composition of the filtered liquid component supplied to the system and of the samples of treated liquid component eluted from the system were analyzed for (among other things) xylose concentration, glucose concentration and furfural concentration. It was observed that the resin retained furfural but did not retain xylose and glucose (which were eluted and comprised in the treated liquid component). The results are shown in TABLE 7C and FIG. 13B.

The embodiments as disclosed and described in the application (including the FIGURES and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

TABLE 1A

| | | | | | | | | | |
|---|---|---|---|---|---|---|---|---|---|
| Biomass Composition ||||||||||
| | Husks/ | | Cellulose | Hemicellulose |||| | |
| Cob (percent) | Leaves (percent) | Stalk (percent) | (Glucan) (percent) | Xylan (percent) | Arabinan (percent) | Acetate (percent) | Composite (percent) | Lignin (percent) | Ash (percent) |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |

TABLE 1A-continued

Biomass Composition

| Cob (percent) | Husks/Leaves (percent) | Stalk (percent) | Cellulose (Glucan) (percent) | Xylan (percent) | Arabinan (percent) | Acetate (percent) | Hemicellulose Composite (percent) | Lignin (percent) | Ash (percent) |
|---|---|---|---|---|---|---|---|---|---|
| 0 | 0 | 100 | 41.7 | 22.5 | 2.4 | 2.6 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

TABLE 1B

Biomass Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-8 |
| Expected Range | 30-55 | 20-50 | 10-25 | 1-10 |

TABLE 2A

Pre-Treated Biomass Liquid Component Composition

| Cob (percent) | Husks/Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 30 | 50 | 20 | 0.4 | 3.6 | 0.5 | 4763 |

TABLE 2B

Pre-Treated Biomass Liquid Component Typical and Expected Composition

| | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

TABLE 3A

Pre-Treated Biomass Solids Component Composition

| Cob (percent) | Husks/Leaves (percent) | Stalk (percent) | Cellulose (Glucan) (percent) | Xylan (percent) | Arabinan (percent) | Acetate (percent) | Hemicellulose Composite (percent) | Lignin (percent) | Ash (percent) |
|---|---|---|---|---|---|---|---|---|---|
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 30 | 50 | 20 | 55.5 | 3.8 | 0.8 | 0.6 | 11.5 | 25.4 | 5.8 |

TABLE 3B

Pre-Treated Biomass Solids Component Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

TABLE 4

| Sample Description | Glucose (percent) | Xylose (percent) | Furfural (ppm) |
|---|---|---|---|
| Starting material (Liquid Component C5) | 0.63 | 4.50 | 1266 |
| Optipore SD2, 1 g per 50 mL | 0.42 | 4.38 | 777 |
| Optipore SD2, 5 g per 50 mL | 0.42 | 4.30 | 269 |
| Optipore SD2, 10 g per 50 mL | 0.41 | 3.93 | 72 |
| Optipore SD2, 20 g per 50 mL | 0.41 | 3.45 | 24 |

TABLE 5A

| Volume Eluted (mL) | Xylose (percent) | Glucose (percent) | Furfural (ppm) |
|---|---|---|---|
| 0 | 4.50 | 0.63 | 1266 |
| 100 | 0.28 | — | 22 |
| 150 | 1.21 | 0.40 | 23 |
| 200 | 2.26 | 0.49 | 26 |
| 250 | 3.10 | 0.54 | 32 |
| 300 | 3.58 | 0.57 | 36 |
| 350 | 4.03 | 0.60 | 43 |
| 400 | 4.28 | 0.62 | 49 |
| 450 | 4.39 | 0.63 | 60 |
| 500 | 4.38 | 0.60 | 69 |
| 550 | 4.47 | 0.62 | 85 |
| 600 | 4.54 | 0.62 | 98 |
| 650 | 4.66 | 0.65 | 115 |
| 700 | 4.66 | 0.66 | 130 |
| 750 | 4.61 | 0.63 | 149 |
| 800 | 4.59 | 0.64 | 168 |
| 850 | 4.56 | 0.64 | 186 |
| 900 | 4.59 | 0.64 | 207 |
| 950 | 4.34 | 0.62 | 222 |

TABLE 5B

| Resin | Optipore SD-2 |
|---|---|
| Bed Volume | 100 mL |
| Bed Height: Diameter Ratio | 4:1 |
| Column Feed and Elution Rate | 37-43 mL/min |

TABLE 5C

| Volume Eluted (mL) | Xylose (percent) | Furfural (ppm) | Ethanol Produced (percent) |
|---|---|---|---|
| 450 | 0.92 | 0 | 0.28 |
| 950 | 1.98 | 138 | 1.10 |
| 1450 | 1.97 | 191 | 1.05 |
| 1950 | 1.97 | 261 | 1.07 |
| 2450 | 1.99 | 310 | 1.12 |
| 2950 | 2.04 | 391 | 1.10 |
| 3450 | 1.98 | 462 | 1.14 |
| 3950 | 1.98 | 525 | 1.09 |
| 4450 | 1.99 | 578 | 1.09 |
| 4950 | 2.00 | 593 | 1.15 |
| 5450 | 1.93 | 568 | 1.10 |
| 5950 | 1.93 | 701 | 1.10 |
| 6450 | 1.97 | 699 | 1.08 |
| 6950 | 1.97 | 718 | 1.11 |

TABLE 5D

| Resin | Optipore SD-2 |
|---|---|
| Bed Volume | 100 mL |
| Bed Height: Diameter Ratio | 4:1 |
| Column Feed and Elution Rate | 75 ml/min |
| Fractions Collected | 1 L every 7 liters eluted |

TABLE 5E

| Fraction | Furfural (ppm) | Xylose (percent) | | | | Ethanol (percent) | | | |
|---|---|---|---|---|---|---|---|---|---|
| | 0 h | 0 h | 24 h | 48 h | 72 h | 0 h | 24 h | 48 h | 72 h |
| 1 | 856 | 4.29 | 3.68 | 0.52 | 0.11 | 0.00 | 0.42 | 2.20 | 2.29 |
| 2 | 913 | 4.37 | 3.99 | 1.57 | 0.15 | 0.00 | 0.30 | 1.60 | 2.38 |
| 3 | 902 | 4.35 | 4.05 | 2.09 | 0.17 | 0.00 | 0.29 | 1.31 | 2.41 |
| 4 | 911 | 4.38 | 4.10 | 2.71 | 0.18 | 0.00 | 0.26 | 0.94 | 2.40 |
| 5 | 955 | 4.46 | 4.25 | 3.58 | 0.54 | 0.00 | 0.24 | 0.55 | 2.28 |
| 6 | 970 | 4.55 | 4.39 | 3.63 | 0.58 | 0.00 | 0.24 | 0.54 | 2.21 |
| 7 | 949 | 4.30 | 4.20 | 3.25 | 0.37 | 0.00 | 0.23 | 0.63 | 2.28 |
| 8 | 958 | 4.36 | 4.15 | 2.91 | 0.21 | 0.00 | 0.25 | 0.81 | 2.39 |
| 9 | 914 | 4.39 | 4.10 | 2.20 | 0.17 | 0.00 | 0.28 | 1.23 | 2.43 |
| Control | 912 | 4.34 | 4.14 | 4.15 | 4.14 | 0.00 | 0.04 | 0.05 | 0.05 |

TABLE 5F

| Resin | Optipore SD-2 |
|---|---|
| Bed Volume | 100 mL |
| Bed Height: Diameter Ratio | 4:1 |
| Column Feed and Elution Rate | 75 mL/min |
| Fractions Collected | 1 L per fraction, 1 L per wash |

TABLE 5G

| Fraction Volume (mL) | Vol. Eluted (mL) | Xylose (percent w/v) | Furfural (ppm) |
|---|---|---|---|
| 10 | 0 | 4.52 | 1239 |
| 1000 | 1000 | 3.64 | 502 |
| 1000 | 2000 | 4.58 | 920 |
| 1000 | 7000 | 4.55 | 1268 |
| 1000 | H2O wash | 0.35 | 222 |
| 1000 | NaOH wash | 0.03 | 8 |
| 1000 | H2O wash | 0.01 | 22 |
| 1000 | 8000 | 3.50 | 377 |
| 1000 | 9000 | 4.53 | 827 |
| 1000 | 14000 | 4.23 | 950 |
| 1000 | H2O wash | 0.32 | 412 |
| 1000 | NaOH wash | 0.02 | 4 |
| 1000 | H2O wash | 0.00 | 52 |
| 1000 | 15000 | 3.39 | 363 |
| 1000 | 16000 | 4.25 | 615 |
| 1000 | 21000 | 4.15 | 1004 |
| 1000 | H2O wash | 0.56 | 580 |
| 1000 | NaOH wash | 0.02 | 4 |
| 1000 | H2O wash | 0.00 | 32 |
| 1000 | H2O wash | 0.01 | 102 |

TABLE 6A

| Sample Description | Glucose (percent) | Xylose (percent) | Furfural (ppm) |
|---|---|---|---|
| Starting material (Liquid Component C5) | 0.63 | 4.50 | 1266 |
| Dowex Optipore L493, 1 g per 50 ml | 0.20 | 2.12 | 334 |
| Dowex Optipore L493, 5 g per 50 ml | 0.17 | 2.00 | 47 |
| Dowex Optipore L493, 10 g per 50 ml | 0.25 | 2.58 | 20 |
| Dowex Optipore L493, 20 g per 50 ml | 0.27 | 2.82 | 10 |

TABLE 6B

| Resin | Optipore L493 |
|---|---|
| Bed Volume | 100 mL |
| Bed Height: Diameter Ratio | 10:1 |
| Column Feed and Elution Rate | 40-50 mL/min |

TABLE 6C

| Volume Eluted (mL) | Xylose (percent) | Glucose (percent) | Furfural (ppm) |
|---|---|---|---|
| 0 | 4.24 | 0.41 | 586 |
| 100 | 0.02 | — | 2 |

TABLE 6C-continued

| Volume Eluted (mL) | Xylose (percent) | Glucose (percent) | Furfural (ppm) |
|---|---|---|---|
| 150 | 0.48 | 0.06 | 2 |
| 200 | 1.71 | 0.19 | 9 |
| 250 | 2.93 | 0.30 | 7 |
| 300 | 3.57 | 0.36 | 8 |
| 350 | 3.89 | 0.38 | 9 |
| 400 | 4.09 | 0.40 | 9 |
| 450 | 4.10 | 0.39 | 10 |
| 500 | 4.18 | 0.39 | 6 |
| 550 | 4.25 | 0.41 | 12 |
| 600 | 4.26 | 0.41 | 13 |
| 650 | 4.30 | 0.41 | 14 |
| 700 | 4.27 | 0.41 | 11 |
| 750 | 4.29 | 0.41 | 13 |
| 800 | 4.23 | 0.41 | 13 |
| 850 | 4.31 | 0.41 | 14 |
| 900 | 4.29 | 0.42 | 16 |
| 950 | 4.25 | 0.41 | 17 |

TABLE 7A

| Sample Description | Glucose (percent) | Xylose (percent) | Furfural (ppm) |
|---|---|---|---|
| Starting material (Liquid Component C5) | 0.63 | 4.50 | 1266 |
| Purolite MN102, 1 g per 50 ml | 0.32 | 3.35 | 592 |
| Purolite MN102, 5 g per 50 ml | not analyzed | not analyzed | 136 |
| Purolite MN102, 10 g per 50 ml | 0.33 | 3.23 | 29 |
| Purolite MN102, 20 g per 50 ml | 0.31 | 3.03 | 7.9 |

TABLE 7B

| | |
|---|---|
| Resin | Purolite MN-102 |
| Bed Volume | 100 mL |
| Bed Height: Diameter Ratio | 4:1 |
| Column Feed and Elution Rate | 40-50 mL/min |

TABLE 7C

| Volume Eluted (mL) | Xylose (percent) | Glucose (percent) | Furfural (ppm) |
|---|---|---|---|
| 0 | 4.21 | 0.41 | 546 |
| 100 | — | — | 1.9 |
| 150 | 0.19 | 0.01 | 1.9 |
| 200 | 1.23 | 0.09 | 1.9 |
| 250 | 2.53 | 0.25 | 1.9 |
| 300 | 3.28 | 0.32 | 1.9 |
| 350 | 3.65 | 0.35 | 5.3 |
| 400 | 3.92 | 0.38 | 1.9 |
| 450 | 4.07 | 0.40 | 13 |
| 500 | 4.13 | 0.39 | 11 |
| 550 | 4.20 | 0.40 | 12 |
| 600 | 4.19 | 0.40 | 14 |
| 650 | 4.33 | 0.41 | 16 |
| 700 | 4.25 | 0.41 | 16 |
| 750 | 4.20 | 0.40 | 19 |
| 800 | 4.21 | 0.41 | 24 |
| 850 | 4.21 | 0.41 | 27 |
| 900 | 4.21 | 0.40 | 25 |
| 950 | 4.21 | 0.40 | 28 |

We claim:

1. A system for the production of ethanol from pre-treated biomass comprising:
   a source of pre-treated biomass;
   a centrifuge in fluid communication with the source of pre-treated biomass, wherein the centrifuge is configured to separate the pre-treated biomass into a liquid component and a solid component, wherein the liquid component comprises sugars;
   a filter comprising a pore size of between 25 microns and 100 microns, wherein the filter is in fluid communication with the centrifuge to receive the liquid component to provide a filtered liquid component;
   an apparatus configured to remove one or more inhibitors from the filtered liquid component, thereby yielding a first treated liquid component, wherein the apparatus is in fluid communication with the filter to receive the filtered liquid component;
   an evaporation system in fluid communication with the apparatus to receive the first treated liquid component to remove water from the first treated liquid component and produce a second treated liquid component; and
   a fermentation system in fluid communication with the evaporation system to receive the second treated liquid component, wherein the fermentation system comprises an ethanologen to ferment the sugars into ethanol;
   wherein the apparatus comprises an ion exchange system comprising a resin bed;
   wherein the resin bed comprises a resin capable of binding said inhibitors;
   wherein the biomass comprises lignocellulosic material;
   wherein the lignocellulosic material comprises at least one of corn cobs, corn plant husks, corn plant leaves and corn plant stalks.

2. The system of claim 1 wherein the inhibitors comprise furfural.

3. The system of claim 1 wherein the inhibitors comprise hydroxymethylfurfural.

4. The system of claim 1 wherein the liquid component comprises furfural in a concentration of at least 700 PPM.

5. The system of claim 1 wherein the resin does not retain sugars.

6. The system of claim 1 wherein the resin does not retain xylose.

7. The system of claim 1 wherein the first treated liquid component comprises furfural at a concentration of no more than 700 PPM.

8. The system of claim 1 wherein the first treated liquid component comprises hydroxymethylfurfural at a concentration of no more than 100 PPM.

9. The system of claim 1 wherein the resin comprises an ion exchange chromatography type resin.

10. The system of claim 1, wherein the ion exchange system is in fluid communication with a source of a caustic solution and the filtered liquid component, and wherein the ion exchange system is configured to regenerate the resin bed by washing the resin bed with caustic solution from the source of caustic solution.

11. The system of claim 10, wherein the ion exchange system comprises:
    a first column comprising a resin bed; and
    a second column comprising a resin bed,
    wherein the first column and the second column are each in fluid communication with the source of a caustic solution and the filtered liquid component, and wherein the first column and the second column are each configured to regenerate the resin bed by washing the resin bed with caustic solution from the source of caustic solution.

12. The system of claim 11, wherein the first column and the second column are configured in a parallel flow arrangement.

* * * * *